(12) United States Patent
DuGal

(10) Patent No.: US 7,986,821 B2
(45) Date of Patent: Jul. 26, 2011

(54) PROCESSES AND APPARATUS FOR IMAGING PROTOCOLS AND ANALYSIS

(75) Inventor: Tiffany Ann DuGal, Mukwonago, WI (US)

(73) Assignee: General Electric Company, Schenectady, NY (US)

( * ) Notice: Subject to any disclaimer, the term of this patent is extended or adjusted under 35 U.S.C. 154(b) by 944 days.

(21) Appl. No.: 11/504,520

(22) Filed: Aug. 15, 2006

(65) Prior Publication Data

US 2008/0044069 A1    Feb. 21, 2008

(51) Int. Cl.
*G06K 9/00* (2006.01)
*G06F 3/00* (2006.01)

(52) U.S. Cl. ....................... 382/128; 715/700

(58) Field of Classification Search .......... 382/128–132; 345/424, 422; 715/700

See application file for complete search history.

(56) References Cited

U.S. PATENT DOCUMENTS

| | | | |
|---|---|---|---|
| 5,678,570 A * | 10/1997 | Manning | 128/897 |
| 5,986,662 A * | 11/1999 | Argiro et al. | 345/424 |
| 7,324,675 B2 * | 1/2008 | Raman et al. | 382/128 |
| 2004/0087850 A1 * | 5/2004 | Okerlund et al. | 600/407 |

* cited by examiner

*Primary Examiner* — Vu Le
*Assistant Examiner* — Amara Abdi
(74) *Attorney, Agent, or Firm* — Rick Wascher, Esq.; Michael G. Smith, Esq.

(57) ABSTRACT

Systems, processes and apparatus are described through which signals are modified within a system. A process for image conditioning in a nondestructive imaging system includes acts of: (i) selecting a protocol from a group of protocols, each protocol of the group being structured to provide multiple coordinated views of a particularized anatomical region and to facilitate automated characterization of an aspect of the anatomical region; (ii) opting for at least one of a plurality of viewing modalities for review of images associated with the selected protocol; and (iii) displaying the images in conformance with the at least one viewing modality.

7 Claims, 17 Drawing Sheets

PROCESSES AND APPARATUS FOR IMAGING PROTOCOLS AND ANALYSIS

FIELD OF THE DISCLOSURE

This disclosure relates generally to concerns involving augmenting or streamlining imaging capabilities of existing systems, in particular to protocols useful in realizing efficient display and analysis of images in imaging systems, and, more particularly, to techniques for facilitating such in a context of multidimensional imaging apparatus, including tools employed in medical diagnosis.

BACKGROUND

Many medical diagnoses rely on non-invasive diagnostic tools to provide information, often in the form of images, descriptive of status of internal portions or organs of a patient. These tools include thermal imaging (e.g., mammography), ultrasonic probes, magnetic resonance imaging techniques, positron emission tomography, computed tomography (CT), single photon emission-computed tomography (SPECT) and optical imaging and/or X-ray-based techniques. In some minimally invasive instances, imaging aids, such as contrast-enhancing agents, are introduced into the subject or patient to aid in increasing available data content from the non-destructive imaging technique or techniques being employed.

Each of these tools presents advantages in particularized situations, has technological limitations, may require set-up and analysis time, can include risks and also has associated costs. As a result, a cost-benefit analysis that also reflects the degree of urgency with respect to a particular diagnostic trajectory often favors usage of X-ray-based measurement techniques.

Several factors influence image quality resulting from an X-ray procedure. Statistical photon noise resulting from characteristics of the X-ray source and the X-ray generation conditions tends to dominate other noise sources in formation of an X-ray-based image. Signal conditioning consistent with achieving suitable contrast between various image portions, and contrast enhancement techniques, are also important considerations in providing diagnostic images, and these issues require increasingly sophisticated treatment as dose and/or photon energy are decreased.

One of the key tenets of medical X-ray imaging is that image quality should be carefully considered in determining exposure conditions. Exposure considerations include predetermined dose criteria vis-á-vis the dose of X-ray delivered to the test subject or patient in order to provide images. The design and operation of a detector used for medical X-ray imaging should therefore be tailored, responsive to the particularized task and measurement conditions, including variables in test subject mass, opacity and the like, to provide high image quality for each X-ray exposure that is incident on the detector.

However, diagnostic medical tools such as X-ray-based imaging systems are precision instruments, very carefully designed, and then built to exacting standards. As such, these kinds of imaging systems represent significant capital investments. Additionally, training personnel to maintain and calibrate such equipment, to operate the equipment, and then to interpret data obtained via these diagnostic tools, also encompasses additional investment. Further, comparison of data from one assessment to another, and from one timeframe to another, is greatly facilitated when the data are collected and processed in a relatively well-understood and documented context. At the same time, technical developments may provide opportunity to leverage existing infrastructural elements by retrofitting them using sophisticated, newly-developed technological subsystems, and this also may facilitate capabilities not present in the ensemble of system elements contemplated at initial design and deployment.

For example, X-ray systems and other non-destructive and largely non-invasive characterization devices have realized dramatic changes in capability during the last century or more. Medical diagnostic capabilities unimaginable prior to C. W. Roentgen's observations of X-ray-based images in 1895 have fostered intense and remarkably fruitful research, study and development, improving medical treatment capabilities to such an extent as to have, in turn, played pivotal roles leading to conception and subsequent maturation of entirely new medical specialties and treatment options.

One new tool resulting from this research employs pixelated X-ray detectors (detectors comprising a geometric array of multiple detector elements, where each detector element may be individually representative of at least a portion of a picture element or pixel in the resultant image). These detectors are increasingly being employed, particularly for medical imaging. Among other things, they facilitate digital representation of images and other data resulting from usage of the systems, which, in turn, enables digital signal processing, data storage and data transmission technologies.

A significant result of these technological innovations is that the potential and capability for real-time consultation between multiple experts, such as medical doctors, during what is called the "golden hour" following a medically-significant event, is greatly enhanced. Representation of such information in digital formats eases transmission, reception and standardized display of the information without incurring loss of acuity of data obtained from the measurement process and greatly eases reduction of noise from the transmission/reception process. In turn, this facilitates capability for multiple experts to collaborate virtually instantly, even from geographically diverse locations, despite extreme scenarios, e.g., triage following an unanticipated disaster. As a result, these capabilities represent strong impetus to incorporate new capabilities within existing diagnostic instruments.

Another significant advance in X-ray imaging involves computerized tomography (CT). The term "tomography" is formed via conjunction of tomos (Greek, "section"), and graphia ("describing"). CT techniques rely on collection of a series of pixelated sectional views, or slices, each taken at a slightly different angle vis-à-vis the test subject, usually in conformance with a helical scanning protocol. The resulting digitized data permits a number of different graphical representations of structures or organs within the test subject in conformance with three-dimensional viewing and analysis, and other techniques.

As these new imaging tools have been developed and combined to provide synergistic results, the volume of data resulting from an imaging procedure has grown along with the increasing gamut of capabilities for analyzing, displaying and employing the data. As a result, it is increasingly difficult and time-consuming to examine the many elements of information resulting from an imaging procedure in order to determine and select the vital few elements needed for various highly specialized types of procedures. In turn, this explosion of data results in delay in applying the results from the procedure, and this is particularly felt in situations requiring extremely rapid response to unexpected demand for medical services, such as an influx of many critically-injured patients following one or more traumatic events such as vehicular disasters and the like.

An additional aspect that tends to compound the acuteness of these issues results from the high investment required in order to provide the imaging machines and to engage appropriately-trained staff and physicians in conjunction with that imaging capability as well as the ancillary medical equipment and infrastructure. A consequence of such is that time and effort saved in the course of pre-planned but complex procedures, such as detection and correction of aneurisms and the like, tends to increase the availability of the equipment and/or staff when such unanticipated events result in abrupt, and extremely time-critical, demand for those capabilities.

For the reasons stated above, and for other reasons discussed below, which will become apparent to those skilled in the art upon reading and understanding the present disclosure, there are needs in the art to provide more highly automated image computation engines and protocols for application and usage of such capabilities, in order to streamline gathering of information in support of increasingly stringent and exacting performance and economic standards in settings such as medical instrumentation.

SUMMARY

The above-mentioned shortcomings, disadvantages and problems are addressed herein, which will be understood by reading and studying the following disclosure.

In one aspect, a process for image conditioning in a non-destructive imaging system includes acts of: (i) selecting a protocol from a group of protocols, each protocol of the group being structured to provide multiple coordinated views of a particularized anatomical region and to facilitate automated characterization of an aspect of the anatomical region; (ii) opting for at least one of a plurality of viewing modalities for review of images associated with the selected protocol; and (iii) displaying the images in conformance with the at least one viewing modality.

In another aspect, a graphical user interface is provided. The graphical user interface includes a plurality of image panels, and at least one control panel. The at least one control panel is structured to facilitate selecting a protocol from a group of protocols, each protocol of the group being structured to provide multiple coordinated views of a particularized anatomical region and to facilitate automated characterization of an aspect of the anatomical region, and to allow a clinician to opt for at least one of a plurality of viewing modalities for review of images associated with the selected protocol and to display the images in conformance with the at least one viewing modality.

In a yet another aspect, an article of manufacture comprises a computer-readable medium embodying computer code that includes computer-readable instructions, which, when executed by one or more processors, causes the one or more processors to allow a clinician to select a protocol from a group of protocols, each protocol of the group being structured to provide multiple coordinated views of a particularized anatomical region and to facilitate automated characterization of an aspect of the anatomical region; to opt for at least one of a plurality of viewing modalities for review of images associated with the selected protocol; and to display the images in conformance with the at least one viewing modality.

Systems, processes, and computer-readable media of varying scope are described herein. In addition to the aspects and advantages described in this summary, further aspects and advantages will become apparent by reference to the drawings and by reading the following detailed description.

DETAILED DESCRIPTION

In the following detailed description, reference is made to the accompanying drawings that form a part hereof, and in which are shown, by way of illustration, specific embodiments that may be practiced. These embodiments are described in sufficient detail to enable those skilled in the art to practice the embodiments, and it is to be understood that other embodiments may be utilized, and that logical, mechanical, electrical and other changes may be made, without departing from the scope of the embodiments.

As used herein, the term "illumination" refers to exposure to photons, electromagnetic radiation, X-ray radiation, phonons (e.g., insonification via ultrasound) or other wave phenomena, which do not necessarily correspond to light that is visible to a human eye. Ranges of parameter values described herein are understood to include all subranges falling therewithin. The following detailed description is, therefore, not to be taken in a limiting sense.

The detailed description is divided into six sections. In the first section, a system level overview is described. In the second section, an example of a graphical user interface is described. In the third section, embodiments of protocols are described. In the fourth section, processes capable of utility with the system are described. In the fifth sections, hardware and an operating environment in conjunction with which embodiments may be practiced are described. In the sixth section, a conclusion of the detailed description is provided. A technical effect of the systems and processes described in the disclosed subject matter includes capability for revising multiple displayed images in coordination with one another, responsive to user input instructions such as are provided via the operator console and/or graphical user interface tools of the present disclosure.

§I. System Overview

Figure 1:
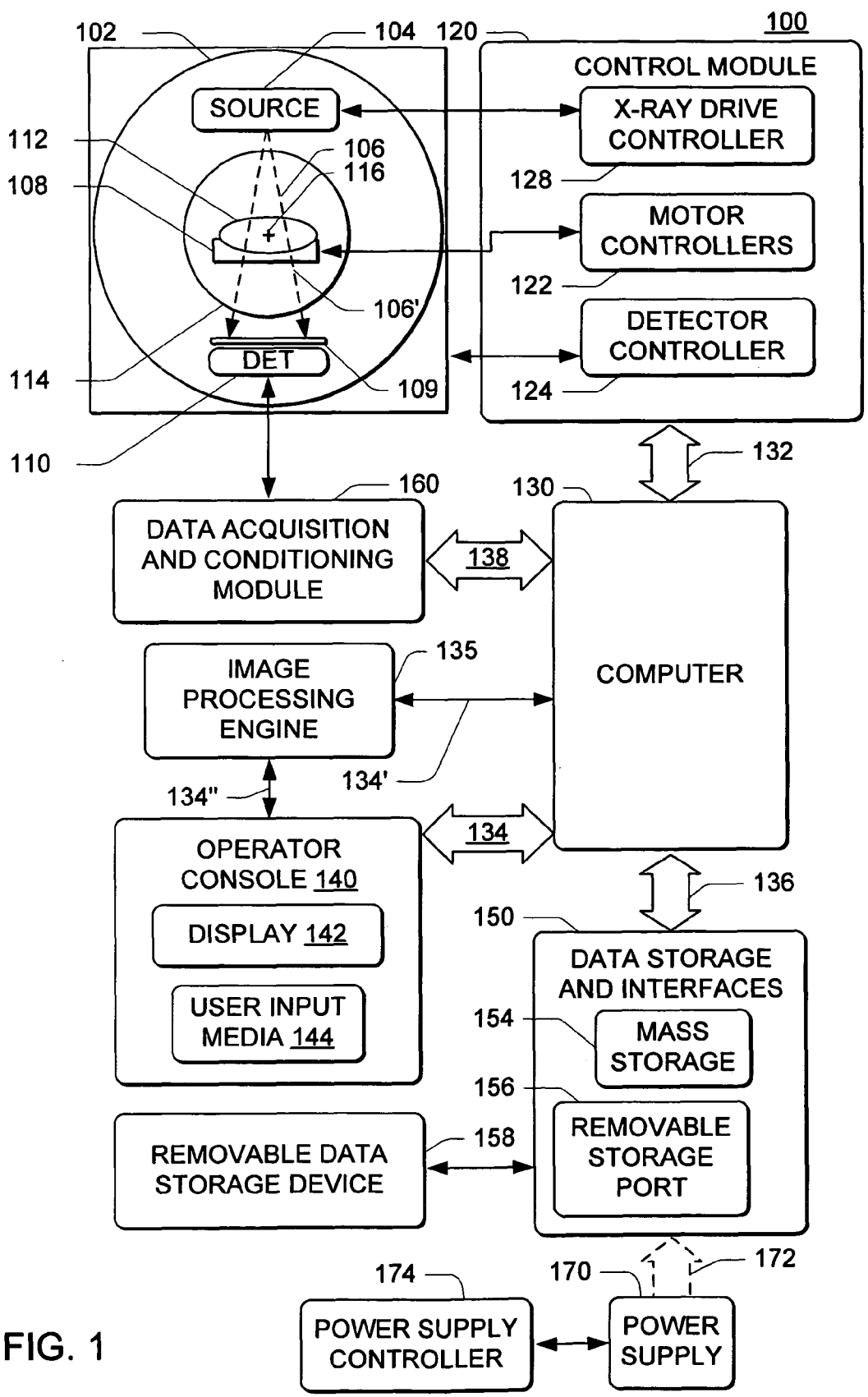
FIG. 1 is a simplified block diagram of an overview of a system configured to improve X-ray imaging operations.

FIG. 1 is a simplified diagram of an overview of a modified system 100 configured to improve X-ray imaging operations. (The system 100 optionally includes a gantry 102 or other support for an illumination source 104, such as an X-ray illumination source, capable of providing illumination 106, such as X-rays or other non-destructive internal imaging illumination, and may optionally include a test subject support 108 that is transmissive with respect to the illumination 106 and that is positioned above a scintillator 109 and detector 110 that is also opposed to the illumination source 104. Alternatively, a direct conversion detector 110 may be employed without need for a scintillator.

In one embodiment, components of the system 100 and a test subject 112 are maintained in a defined geometric relationship to one another by the gantry 102. A distance between the illumination source 104 and the detector 110 may be varied, depending on the type of examination sought, and the angle of the illumination 106 respective to the test subject 112 can be adjusted with respect to the body to be imaged responsive to the nature of imaging desired.

In one embodiment, the test subject support 108 is configured to support and/or cause controlled motion of the test subject 112, such as a living human or animal patient, or other test subject 112 suitable for non-destructive imaging, above the scintillator 109/detector 110 so that illumination 106' is incident thereon after passing through the test subject 112. In turn, information from the detector array 110 describes internal aspects of the test subject 112.

The scintillator 109 may be a conventional CsI scintillator 109, optically coupled to an array of photodiodes (not illustrated), such as a two-dimensional array of photodiodes and suitable control transistors formed using semiconductor material such as amorphous silicon, or any other form of detector 110 suitable for use with the type or types of illumination 106 being employed, such as X-rays. The detector elements are typically tessellated in a mosaic. The scintillator 109 converts incident photons comprising electromagnetic radiation, such as X-rays, from high-energy, high-frequency photons 106', into lower-energy, lower-frequency photons corresponding to spectral sensitivity of the detector elements, in a fashion somewhat analogous to fluorescence, as is commonly known in the context of many visible-light sources in use today. Alternatively, the detector 110 may be formed as a flat-panel array including amorphous Silicon ($\alpha$-Si) active elements, together with either a scintillator layer 109, or a direct converter material such as Cadmium Zinc Telluride (CdZnTe), Mercuric Iodide ($HgI_2$), Lead Iodide ($PbI_2$), or amorphous Selenium ($\alpha$-Se).

In some modes of operation, such as CT, the gantry 102 and test subject support or table 108 cooperatively engage to move the test subject 112 longitudinally, that is, along an axis extending into and out of the plane of FIG. 1 and within an opening 114. In some modes of operation, the gantry 102 rotates the X-ray source 104 and detector 110 about the axis 116, while the support 108 moves longitudinally, to provide a helical series of scans of the test subject 112, where a pitch of the helices is defined as a ratio of a longitudinal distance traveled by the table 108 during a complete revolution of the gantry 102, compared to a length of the detector 110 along the axis 116 of linear motion.

In one embodiment, the detector 110 comprises a floating receptor, that is, a detector 110 that is not coupled to the gantry 102 and that is not associated with a patient table 108. In other words, the floating digital detector is portable and is hence 'floating' with respect to other elements of the system 100, and it is attached to the rest of the system 100 via a tether. The term 'floating' is meant to indicate that its position is completely subject to the user and is not controlled via the gantry 102, table 108 or other system device. In one embodiment, the floating receptor 100 may be postured opposite the source 104 with the test subject 112 being located between the source 104 and the floating receptor 110, by placing the floating receptor 110 beneath the test subject 112, for example.

The system 100 also optionally includes a control module or controller 120. The controller 120 may include a motor control module 122 configured to move the test subject support 108 and thus the test subject 112 relative to the X-ray source 104 and/or detector 110, and may also control motors in the gantry 102 or to position the X-ray illumination source 104 relative to the test subject 112 and/or the detector 110.

The controller 120 includes a detector controller 124 configured to control elements within the detector 110 and to facilitate data transfer therefrom. The controller 120 also includes a drive parameter controller 128 configured to control electrical drive parameters delivered to the X-ray source 104. One or more computers 130 provide connections to the controller 120 via a bus 132 configured for receiving data descriptive of operating conditions and configurations and for supplying appropriate control signals. Buses 134, 134' and 134" act to transfer data and control signals, for example with respect to a module 135, configured as an image processing engine, via interconnections such as 134', 134" that are configured for exchange of signals and data to and/or from the computer 130 as well as other elements of the system 100 and/or external computation or communications resources.

The system 100 also includes a bus 136, a bus 138 and an operator console 140. The operator console 140 is coupled to the system 100 through the bus 134. The operator console 140 includes one or more displays 142 and a user input interface 144. The user input interface 144 may include a keyboard, a mouse or other tactile input device, capability for voice commands and/or other input devices. The one or more displays 142 provide video, symbolic and/or audio information relative to operation of system 100, user-selectable options and images descriptive of the test subject 112, and may display a graphical user interface (e.g., see Section II, infra) for facilitating user selection among various modes of operation and other system settings.

The image processing engine 135 facilitates automation of accurate measurement and assessment. The image processing engine 135 is capable of forming multiple, coordinated images for display, for example via the monitor 142, to provide the types of depictions described below with reference to Section III and associated FIGs. The image processing engine 135 may comprise a separate and distinct module, which may include application-specific integrated circuitry, or may comprise one or more processors coupled with suitable computer-readable program modules, or may comprise a portion of the computer 130 or other computation device.

The system 100 also includes memory devices 150, coupled via the bus 136 to the computer 130 through suitable interfaces. The memory devices 150 include mass data storage capabilities 154 and one or more removable data storage device ports 156. The one or more removable data storage device ports 156 are adapted to detachably couple to portable data memories 158, which may include optical, magnetic and/or semiconductor memories and may have read and/or write capabilities, and which may be volatile or non-volatile devices or may include a combination of the preceding capabilities.

The system 100 further includes a data acquisition and conditioning module 160 that has data inputs coupled to the detector 110 and that is coupled by the bus 138 to the one or more computers 130. The data acquisition and conditioning module 160 includes analog to digital conversion circuitry for capturing analog data from the detector 110 and then converting those data from the detector 110 into digital form, to be supplied to the one or more computers 130 for ultimate display via at least one of the displays 142 and for potential storage in the mass storage device 154 and/or data exchange with remote facilities (not shown in FIG. 1). The acquired image data may be conditioned in either the data acquisition and conditioning module 160 or the one or more computers 130 or both.

The system 100 also includes a power supply 170, coupled via interconnections represented as a power supply bus 172, shown in dashed outline, to other system elements, and a power supply controller 174. In some embodiments, the system 100 is configured to be a mobile system equipped with a portable power supply 170, such as a battery. In other words, the system 100 may comprise a wheeled unit and may be electromotively powered in self-contained fashion, lending physical agility to the ensemble of attributes offered by the system 100.

In some settings, such as an emergency room, articulation of a mobility function may be limited to motion of a system 100 that is generally dedicated to application within that setting, suite or environment. In other settings, such mobility may include scheduled sequential visits to areas such as a cardiac unit, an ICU and other loci, where such imaging capability provides critical assistance, such as when the test subject 112 is not postured in a fashion consistent with movement of the test subject 112 and yet aperiodic variations in work load are not favorable to cost-effective deployment of a system 100 incapable of ready, self-propelled, operator-guided, "at need" physical translation of location. In one embodiment, electrically-powered motors coupled to a drive train effectuate operator-directed motion of the system 100.

As part of initiating data collection and then in the process of analyzing data from the system 100, a clinician will need to interact with the system 100 in order to select a measurement type, to select a data manipulation and display protocol and the like. In part, such interaction may be facilitated via the graphical user interface of FIG. 2 and other user-oriented graphical aspects (FIGS. 3 through 8), as described below in Section II.

§II. Exemplary Graphical User Interface (GUI) and Icons

Figure 2:
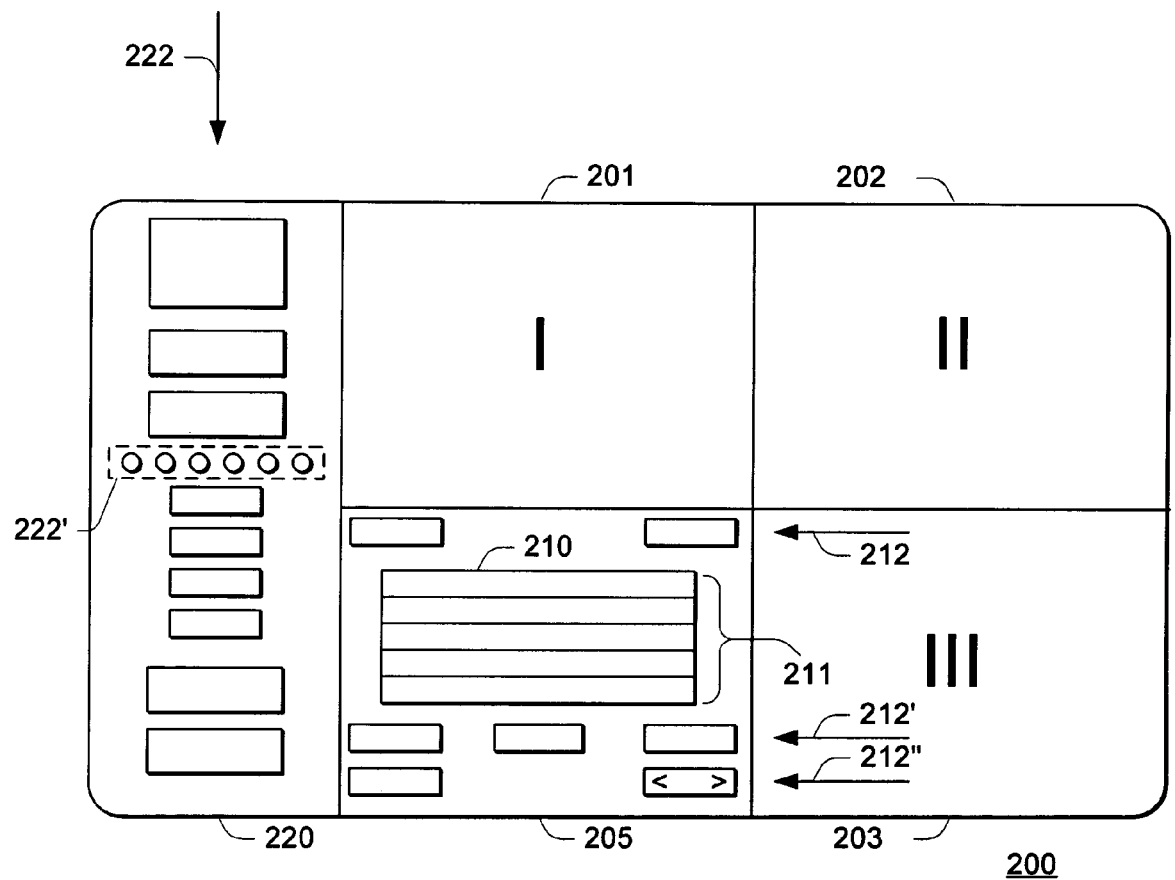
FIG. 2 is a simplified example of a graphical user interface capable of utility in the system of FIG. 1.

FIG. 2 is a simplified illustration showing an example of a graphical user interface 200 capable of utility in the system 100 of FIG. 1. FIGS. 3 through 8 illustrate examples of icons 300 through 800, respectively, associated with a variety protocols described in the present disclosure (see, e.g., Section III, infra).

The graphical user interface 200 includes a first image field 201 for displaying image I, a second image field 202 for displaying image II, a third image field 203 for displaying image III and a control panel or data entry and descriptor field 205.

The control panel or data entry and descriptor field 205 includes a table or list 210 of selected points within an image or body of data, as identified via text labels, for example, in tabular entries 211, and several protocol label and function areas 212, 212', 212". A control function field 220 includes a variety of control buttons, labels and function tools 222 therein.

The graphical user interface 200 is intended to facilitate graceful user interaction in fulfilling several different functions, in an integrated manner. The control panel or data entry and descriptor field 205 may facilitate user interaction with protocol label and function areas 212, 212', 212" including options permitting a selection among functions such as: CLEAR ALL POINTS, ADD BRANCH, EDIT, REMOVE, SAVE PROTOCOL, BACK/NEXT stepping buttons, CROSS OCCLUSION, CONFIGURE PROTOCOL, and other options suitable to the genre or protocol selected.

The control function field 220 permits selection between, among other things, different testing and analysis protocols (described below in Section III with reference to FIGS. 3 through 19), system control functions, and display control functions.

For example, control buttons 222' may be structured to facilitate user input via a tactile input-output device 144 to adjust views displayed on any of image display fields 201, 202, 203 showing image fields or panels I, II, III, respectively, for example, via providing control over clockwise rotation, counter-clockwise rotation, up, down, left and right adjustments, or other translation/rotation functions). Other types of labels and controls may include buttons to allow the user to indicate desire to select a new protocol, to access additional guides, to review steps involved in a given procedure, to select a rotate/translate capability (such as described with reference to the control buttons 222'), to select among, and, generally, manipulate a broad variety of imaging modes and tools.

These options may include, among other things, three-dimensional volume rendering (VR) imaging tools; and three-dimensional min IP and/or MIP imaging tools. In this context, min IP is an acronym associated with minimum intensity projection, and MIP is an acronym associated with maximum intensity projection; each refers to an image enhancement technique that scales intensities nonlinearly to emphasize areas of low radiodensity, such as air sacs, or to emphasize areas of high radiodensity, such as bony materials, respectively.

Other potential tools that the control function field 220 may facilitate invocation of and interaction with can include surface rendering or other edge detection modes; segmentation processes (separation of images of structures having highly similar radiodensity via automated techniques) and other forms of image processing approaches known or used in the relevant arts. Other types of functionality accessible via the function control field 220 may include filming tools; reporting tools; protocol selection tools; and other tools, including system-level tools (e.g., administrative functions, patient or data selection and so forth).

Examples of tactile input/output media include touchscreens, keyboards, switchable rollerball devices, and the like. As well, voice recognition and other forms of input-output functionality may be enabled.

The data entry and descriptor field 205 includes tabular entries 211 in the table 210. These tabular entries 211 may reference points selected or identified for sizing of stents or for other reasons, as described below in more detail with reference to FIGS. 3 through 13, in Section II, below. Buttons in the fields 212, 212', 212" may facilitate access to functions such as HELP data, visual protocol preference selection functions, functions such as clearing of data points, hiding panels, editing functions, adding branches and/or removing items to accommodate individual physiologies, saving data associated with a protocol, and forward and back functions for sequencing through a protocol. The different protocols described in this disclosure may have associated visual symbols, as briefly described below with reference to the examples of FIGS. 3 through 8.

FIGS. 3 through 8 illustrate examples of icons 300 through 800, respectively, associated with a variety protocols described in the present disclosure. The icons 300 through 800 provide symbols intended to provide communication independent of any specific language with respect to operation of the system 100.

Figure 3:
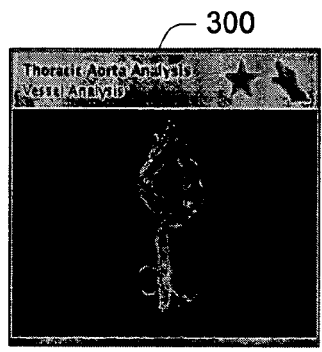
FIGS. 3 through 8 illustrate examples of icons associated with a variety protocols described in the present disclosure.
Figure 6:
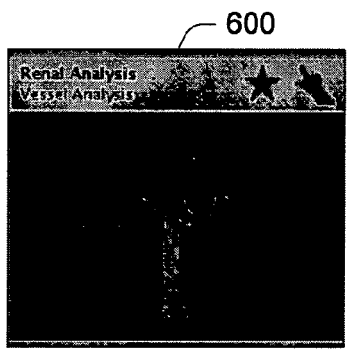
Figure 7:
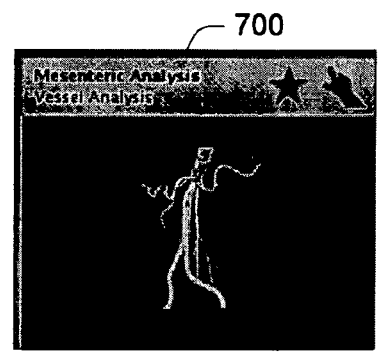
Figure 4:
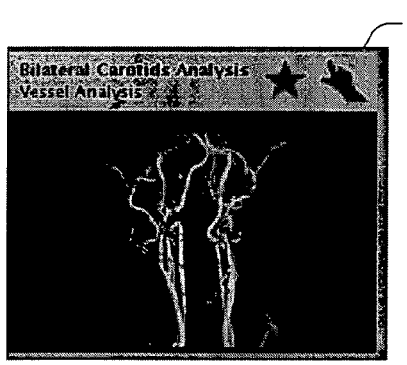
Figure 5:
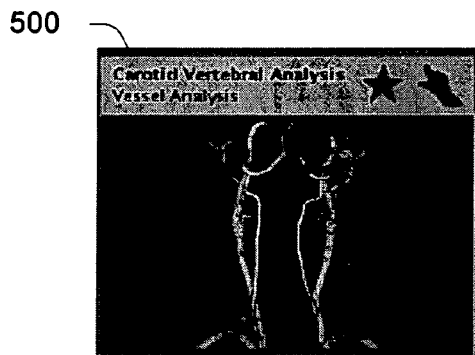
Figure 8:
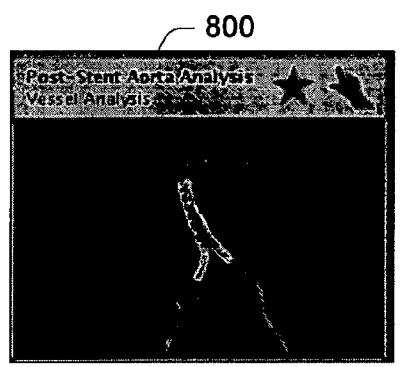

FIG. 3 shows an icon 300 or "thumbnail" indicative of a thoracic aorta analysis protocol, which protocol is described in more detail in subsection III(B) below. FIG. 4 provides an example of an image 400 denoting a bilateral carotid arterial analysis protocol, as is discussed further infra with reference to subsection III(C). FIG. 5 illustrates an iconographic element 500 descriptive of a carotid vertebral analysis protocol, which protocol is more thoroughly exemplified via the description of subsection III(D). FIG. 6 is one example of a thumbnail 600 providing affirmative indication of selection of a renal arterial analysis protocol, as is fleshed out in more detail via the examples contained in subsection III(E) below. FIG. 7 affords a simplified representative image 700 linked to a mesenteric arterial analysis protocol, which is further developed in the context of subsection III(F) following thereafter. FIG. 8 displays an icon 800 providing access to a post-operative comparison protocol that is described in more detail in subsection III(H), following the text descriptive of the specific characterization protocols.

The system 100 of FIG. 1, the graphical user interface 200 of FIG. 2 and the icons 300 through 800 of FIGS. 3 through 8 facilitate a variety of non-invasive characterizations of hard and soft tissues, and of aiding in automated analysis of such to derive information useful in determining sizing and other factors relative to intervention with respect to a variety of medical issues. Several examples of protocols useful in coordinating displays of such data and in facilitating automated characterizations of such, via adaptive system elements, are described below in Section III.

§III. Exemplary Vascular Imaging and Characterization Protocols

In this section, two primary classes of circulatory issues are briefly described. This background is followed by presentation of several exemplary vascular characterization and assessment protocols. In turn, the protocols are implementable via adaptive and programmable aspects applicable to the system 100 of FIG. 1 of Section I, supra. In that context, they are also amenable to facilitating user input, and to providing useful imaging and characterization aspects, via the GUI 200 of FIG. 2 and the iconographic indicia 300 through 800 of FIGS. 3 through 8 of Section II.

It will be appreciated that, while these concepts as disclosed and enabled below are phrased in terms of conventions such as particularized embodiments, other forms of description and other applications are applicable and may be employed, without significantly altering the teachings of the present disclosure. Section III begins with an overview (§III (A)) and then includes several specific applications of the subject matter of the disclosure (§§III(B) et seq.).

§III(A). Overview

The increased capacities for imaging of soft tissues via X-ray techniques, and for providing a range of different, but complementary, imaging and analysis capabilities, result in greatly improved success in applying such tools for detecting and treating many types of conditions or diseases. For example, computerized tomography now is able to provide diagnostic and analytical techniques applicable to several types of serious vascular conditions.

Arterial abnormalities that may result in significant disability and that also may have potentially life-threatening consequences, and which present profiles that have strongly benefited from such imaging advances include, atherosclerosis and aneurysms (or, in lay terms, conditions potentially leading to blockages and blowouts, respectively). More particularly, demand for anatomically-specific protocols for applications in medical areas of treatment involving, e.g., the thoracic aorta, carotid arteries, vertebral arteries, renal arteries, and abdominal mesenteric arteries is increasingly acute. Desire for such new protocols is presently significant in clinical settings, and will only increase as the gamut of diagnostic and treatment options. Past demands in this area have provided some tools for vessel imaging and analysis. However, the utility and practicality of those tools have been rapidly outstripped, as the sophistication of the tools increases, and particularly because the sheer volume of data from such imaging procedures has grown explosively.

This has been particularly true in the context of addressing consequences of vascular disease. Within that area of medical concern, atherosclerosis is the most commonly-encountered form of vascular disease that is noted in many countries.

Atherosclerosis involves the slow buildup of deposits of fatty substances, cholesterol, body cellular waste products, calcium and fibrin in the inside lining of critical vascular structures such as arteries. Atherosclerosis is a leading cause of illness and death, affecting over 60 million people, and has been linked to more deaths per year in the United States than those resulting from cancer or from accidents. Additionally, the populations of many countries display cholesterol levels resulting in high risk for developing some form of vascular disease.

The deposits associated with atherosclerosis can partially or totally occlude a vessel. Portions of the deposits can detach from one site and then lodge in another site, thus causing occlusive strokes. Such deposits are also linked to formation of vascular aneurysms, to myocardial infarction, to renal failure, and also to formation of pulmonary emboli.

Additionally, claudication may cause impairment in the extremities that can result in serious compromise of one or more major life activities. Aspects contributing to such disability may include extreme pain and difficulty walking. Eventually necrosis (gangrene) or other vascular ailments may result from such blockage.

The high mortality rates associated with atherosclerosis, coupled with widespread suffering and enormous economic impact of lost productivity, as well as costs of treatment, collectively present demands for increasingly integrated medical approaches and therapies. As a result, there are strongly-felt desires to promote yet even more sophisticated, advanced, anatomically-specific tools to aid in the diagnosis and treatment of these widespread diseases.

Aneurysms also are able to be imaged via computerized tomographic X-ray techniques. While aneurysms may occur in many places throughout the body, a large fraction of life-threatening conditions treatable with minimally invasive techniques, or where treatment is facilitated through non-invasive measurements, include those of the major arteries of the neck and abdomen.

Thoracic aortic aneurysms predominantly occur in the descending thoracic aorta. However, significant numbers of such aneurysms occur in either the ascending aorta or the aortic arch.

A stent implant ("stenting") may be a desirable treatment option for patients with aneurysms of the descending thoracic aorta. Stenting involves the use of a tube placed inside the vessel and can be performed without a chest incision, by use of specialized catheters that are introduced through arteries at the groin. Physicians performing this type of intervention need a streamlined, fast and easy-to-use, but accurate, protocol for measuring the aorta to provide data in suitable formats, and in conformance with established standards used in such medical practice, in order to customize treatment, such as formulation of a stent, for each patient.

Accordingly, new methods and procedures are being developed for diagnosing and treating vascular disease, contemporaneously with creation of new, and increasingly specialized, imaging equipment and techniques. However, the corresponding increases in the amount of data provided via these modern medical imaging tools also increases dramatically. In turn, an escalating premium is placed on need to be able efficiently sift through the resulting information to identify the vital elements therein, and then to employ such data, also increases.

More particularly, demand for anatomically-specific protocols for applications in medical areas of treatment involving major arteries is increasingly acute. Desire for such new protocols is presently significant in clinical settings, and will only increase as the gamut of diagnostic and treatment options, particularly in the context of addressing consequences of vascular disease. Past demands in this area have provided some tools for vessel imaging and analysis, however, the utility and practicality of those tools have been rapidly outstripped as the sophistication of the tools increases, and particularly as the sheer volume of data from such imaging procedures has grown explosively, in tandem with other advances in the relevant arts.

Several new protocols addressing these needs are described below with reference to FIG. 9 et seq. and associated text. These exemplary protocols include: a thoracic aorta characterization protocol; carotid artery assessment protocols capable of contemporaneous processing and imaging of full bilateral carotid vascularization including vertebral aspects; a renal arterial measurement and display protocol; and a mesenteric artery protocol for data acquisition and analysis relative to the mesenteric and bowel arterial systems. A technical effect of the disclosed subject matter includes benefits such as coordination of multiple images of a region under evaluation such that a selection of two or more of these views may, if desired, be linked to permit the selected displays to all be collectively updated contemporaneously via input made with respect to any one of them.

In one embodiment, such is realized via manipulation of a three-dimensional cursor to identify a point in three-dimensional space that is also common to the subject representations. In other words, a cursor or other user-manipulable/adjustable tool is employable in order to specify a point that is associated with all the selected views.

The selected point corresponds to a location that is associated with the body of tomographic data representing three dimensional characterization of the region under study. As a result, "motion" of the viewer's apparent posture vis-a-vis the region of interest, which motion also may be indicated via user-manipulable techniques, modification of the perspective of one of the images provides automatic, temporally synchronized and dimensionally coordinated revision of all of the selected images.

Within the vessel analysis protocols described in subsection III(B) et seq. described below, all the images or views are capable of being linked via such cursor. As an example, the 3D view of FIG. 12, which displays an image of the vessel as though it was unfolded along a local central axis within the vessel (i.e., as though the central axis had been "straightened"—as in pulling a string to render it one-dimensional) and includes a representation of a cursor line that allows a user to correlate the lumen view with the other views. This horizontal, graduated cursor line, on the view, indicates the intersection with the plane containing the 3D cursor and is displayed in the oblique cross-sectional view of FIG. 11.

Figure 12:
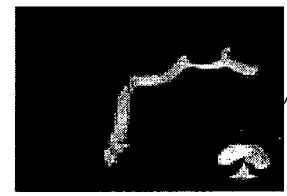

In addition to the view of FIG. 12, the clinician can achieve an effect of moving along the centerline in steps by means of the left and right arrow buttons on the keyboard, depressing the "control" button on the keyboard and then moving the mouse in a north/south fashion, or also by using the left mouse button by selecting the paging button located on the review controller. More detailed discussion follows, with reference to FIG. 9 et seq., considered in conjunction with other aspects of the disclosure, such as the processes 3000 and 3100, noted infra, with respect to Section IV.

§III(B). Thoracic Aorta Characterization Protocol Example

FIGS. 9, 10, 11 and 12 depict multiple, contemporaneous, albeit differing, graphical representations 900, 1000, 1100 and 1200, respectively, showing illustrative data relative to an example of a thoracic aortal characterization protocol. The thoracic aorta characterization protocol, and images associated with it, may be recognized via association with a symbol such as the icon 300 or "thumbnail" of FIG. 3, without requirement for text specific to any particular language.

Figure 9:
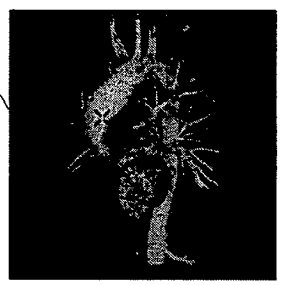
FIGS. 9 through 12 depict multiple, contemporaneous, albeit differing, graphical representations of comprehensive data relative to a thoracic aorta protocol, collected via non-destructive imaging techniques and coordinated in accordance with the image and data processing engines and protocols of the present disclosure, which data organizational, analysis and presentation modalities find utility in the context of the system of FIG. 1.

FIG. 9 provides an example 900 of a three-dimensional rendering of thoracic vascular structures, which may be displayed, for example, via the display 140 of FIG. 1.

Figure 10:
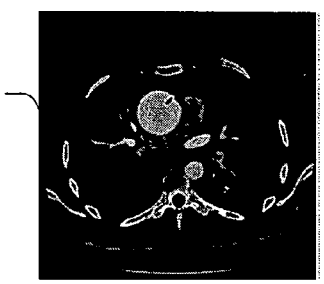
Figure 11:
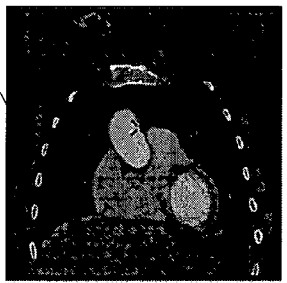

FIG. 10 includes a simplified representation of an axial view 1000 of the structure denoted via the "x" shown slightly above, and left of center of, the rendering shown in FIG. 9. FIG. 11 is a simplified, enlarged oblique cross-sectional illustration 1100 of the structure described above. FIG. 12 is a simplified, enlarged and flattened illustration 1200 of the structure described above.

The coordinated images 900 through 1200 of FIGS. 9 through 12 are formed from a single body of tomographic X-ray data by the image processing engine 135 of FIG. 1. As a result, these may be linked such that modification of parameters (such as viewing angle) associated with at least one of the images is reflected, via appropriate and automatic updating, of images such as those of the others of the FIGs., in order to seamlessly provide images presenting a coherent collective body of visual displays for the clinician.

The data employed in order to be able to construct the representations 900 through 1200 of FIGS. 9 through 12, respectively, may be collected in one or more pre-programmed, i.e., "canned" routines, and, as such, the resulting body of information lends itself to presentation of the views of FIGS. 9 through 12 via one or more aspects of the monitor 142 of FIG. 1, and in coordinated fashion. In other words, when the clinician determines that benefit may result from re-organization of the already-assembled body of data to provide a different angle of view or other parameter variation, relative to that of the view of any of FIG. 9 et seq., it is helpful to enable the practitioner to have, as an option, capacity for contemporaneously readjusting one or more of the displays noted above, in coordinated fashion, with respect to the revised posture of contemplation. Accomplishing such in real time, and without undue burden to the medical analyst, is particularly useful.

For patients with thoracic aorta aneurysms larger than six centimeters in diameter, primary treatment options include replacement of the affected section of the aorta with a fabric substitute, or the affected aorta region can be stented. The thoracic aorta protocol disclosed herein finds utility in assisting clinicians performing thoracic aorta stenting. Often, when it is necessary to measure/characterize a thoracic aorta for an invasive stent placement procedure, the data collection and analysis involves a very time-consuming manual process. As data collection capabilities expand, the number of CT slices and the volume of data available tend to complicate this assessment.

Clinicians performing this type of interventional procedure benefit from a streamlined, rapid and easy-to-use protocol for measuring/characterizing the aorta and then deriving and delivering the required stent sizing data and measurements. In turn, this facilitates any needed customization of the stent size parameters for each patient, for example, to reduce risk of endoleaks and/or ruptures. The protocol dramatically improves both productivity and confidence, resulting in a faster diagnosis and treatment for the patient.

The thoracic aorta protocol rapidly and automatically generates all images appropriate to the protocol. The disclosed protocol also efficiently provides key measurements based on those images, in order to specify stent size for each patient or emplacement, or to provide other pre-operative or post-operative quantitative data as determined to be desirable.

Stent manufacturers (and other suppliers of surgically-related implements) have specified particular measurements needed in order to provide an appropriate stent for the application under contemplation. The disclosed thoracic aorta protocol rapidly, and with minimal demand on medical personnel, readily sorts, analyzes and formats data for these measurements. Descriptions of assessment points and lists of measurements created by these disclosed protocols are presented Tables I, II and III below.

TABLE I

Automatic thoracic aorta protocol measurements.

A). Proximal neck length (subclavian artery origin to aneurysm).
B). Distal neck length (aneurysm to celiac artery).

TABLE II

Data derived from the automatic length measurements.

A). Aneurysm length (aneurysm start and end points).
B). Treatment length (20 mm proximal and 20 mm distal points).

TABLE III

Data derived from automatic diameter measurements.

A). Proximal implantation site diameter characterization*.
   i). One cm from the proximal implantation site.
   ii). Two centimeters from the proximal implantation site.
B). Automatic aneurysm characterization (distal to the proximal implantation site).
   i). Two cm from the distal implantation site.
   ii). One cm from the distal implantation site.

*The proximal implantation site is 20 mm above the aneurysm.

§III(C). Bilateral Carotid Artery Characterization Protocol Example

Prior art left or right carotid artery imaging and measurement protocols do not allow a physician or clinician to track all parts of the carotid arterial system via a single procedural aspect. Instead, these conventional processes sequentially track (with respect to a first side of the patient) the common carotid artery, then the internal carotid artery, then the external carotid artery, which procedures are then repeated for the other side of the neck.

FIGS. 13 through 16 display contemporaneous alternative views 1300 through 1600 of comprehensive imaging information for the bilateral carotid arterial system, after processing by the image and data processing engine 135 and display 142 apparatus and modalities of the present disclosure, exemplifying one way in which the disclosed data organizational, analysis and presentation capabilities find utility in the imaging system 100 of FIG. 1. The bilateral carotid arterial protocol, and images associated with it, may be visually recognized via association with the symbolic image 400 of FIG. 4, without requirement for text specific to any particular language.

Figure 13:
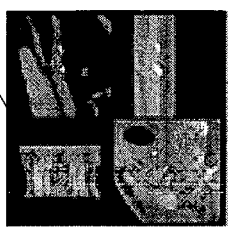
FIGS. 13 through 17 display alternative views of comprehensive imaging information with respect to carotid imaging, after processing by the image and data processing and display apparatus and modalities of the present disclosure, exemplifying ways in which the disclosed capabilities find utility in the imaging system of FIG. 1.

FIG. 13 is a composite 1300 of multiple and distinct image formulations for the carotid arterial system in conformance with the present disclosure. The automated bilateral carotid artery assessment protocol disclosed herein provides capability for collectively tracking all these arteries, right and left, in a single, rapid, robust and accurate, easily-used protocol, providing increased productivity, confidence and overall satisfaction, and also realizing benefits via promoting accessibility of the related imaging equipment and the clinicians to address urgent, but unexpected, demands for critical medical intervention, when needed.

Figure 14:
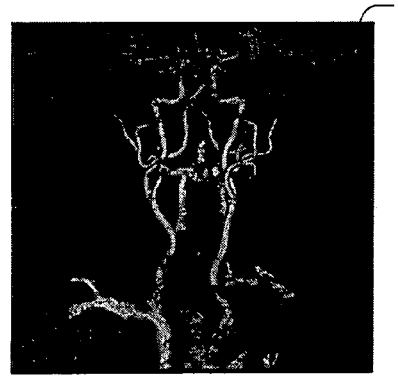
Figure 15:
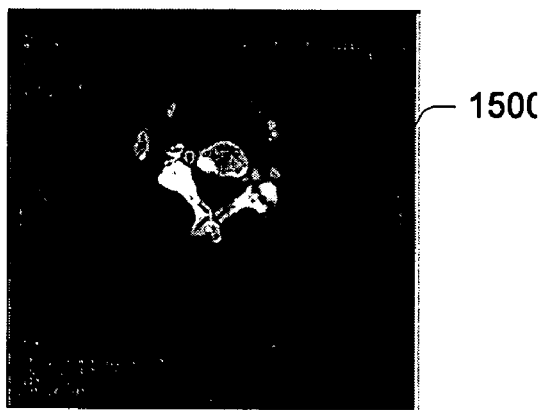
Figure 16:
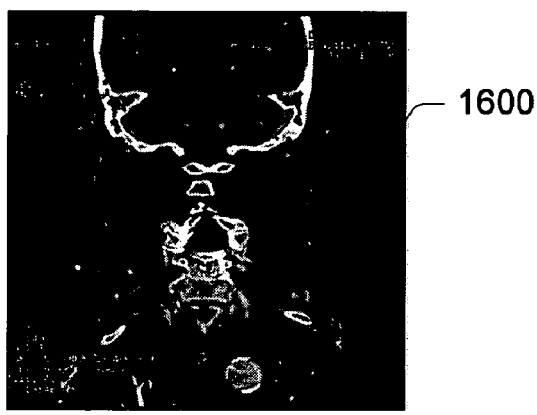

FIG. 14 is an example of a three dimensional volume rendering 1400 of the bilateral carotid arterial system. FIG. 15 is an axial image depiction 1500 for the bilateral carotid arterial system of FIG. 14. FIG. 16 is an example of a coronal view 1600 for the bilateral carotid characterization protocol.

In one embodiment, the 3-D, VR image 1400 of FIG. 14 forms an element such as the first image field or panel I of FIG. 2, while the axial image 1500 of FIG. 15 forms another element such as the second image field or panel II and the coronal image 1600 of FIG. 16 forms the third image field or panel III. In such an instance, the control panel 205 and 210 might have a list of selected points, as exemplified below in Table IV.

TABLE IV

Entries in the table 210 for a composite of FIGS. 9 and 10.

| Line | Point | Abbrev. |
|---|---|---|
| 1 | Start of Section | Start |
| 2 | Brachiocephalic trunk | Brachio |
| 3 | Right Common carotid | Rt Com Car |
| 4 | Right Internal Carotid Artery | Rt Internal |
| 5 | Right External Carotid Artery | Rt Internal |
| 6 | Left Common Carotid | Lt Com Car |
| 7 | Left Internal Carotid Artery | Lt Internal |
| 8 | Left External Carotid Artery | Lt External |

In Table IV, the entries for "line" correspond to enumeration of the lines in the table 210 from the top line (line 1) down; the entries for "point" correspond to locations of points emplaced on the data, and the entries for "abbrev." provide abbreviations that may be used to represent the points but with fewer alphanumeric characters than are used in the labels under the column heading "point." It will be appreciated that other, similar tables may be constructed which are descriptive of elements of other protocols. A list of vessel tracking points useful in the context of the bilateral carotid arterial characterization protocol is provided below in Table V.

TABLE V

Vessel Tracking points for Bilateral Carotids Protocol.

Aortic Arch - Common Start Point
    Brachiocephalic trunk (Innominate)
Right Common Carotid
    Right Internal Carotid Artery
    Right External Carotid Artery
Left Common Carotid
    Left Internal Carotid Artery
    Left External Carotid Artery §III(D). Carotid/Vertebral Artery Characterization Protocol Example Clinicians may wish to evaluate the carotid arteries via one protocol, but this also often involves need to analyze arteries running through the vertebrae in the neck. It is not uncommon for these arteries to also have disease or become damaged from trauma, and, as a result, it is helpful to have a specific protocol to quantify this scenario, and to employ automated characterization tools, in order to promote objective, repeatable assessment techniques.

Figure 17:
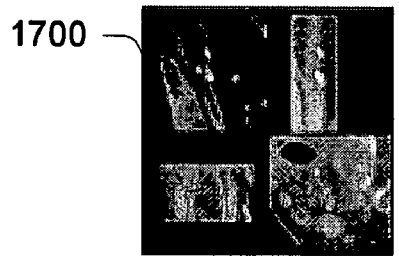

FIG. 17 is a composite 1700 of several different image types rendered from tomographic data by the image processing engine 135 of FIG. 1 for the vertebral carotid arterial system, realized as described above with reference to FIG. 9 et seq., as well as Tables I et seq. and associated text. The vertebral carotid arterial protocol, and images associated with it, may be optically identified via association with the iconographic image 500 of FIG. 5, without requirement for text specific to any particular language.

Such tools also act to efficiently provide robust and repeatable measurements, and to reduce human factor influences (differences in perceptions and in characterization criteria and so forth). An enumeration of some vessel tracking points useful in the context of the carotid/vertebral arterial assessment protocol is provided in Table VI below.

TABLE VI

Vessel Tracking points for Carotid/Vertebral Protocol.

Ascending Aorta
Left Subclavian Artery
Left Common Carotid
Left Internal Carotid Artery
Left External Carotid Artery
Left Vertebral Artery
Brachiocephalic trunk (Innominate)
Right Common Carotid
Right Internal Carotid Artery
Right External Carotid Artery
Right Vertebral Artery §III(E). Renal Artery Characterization Protocol Example Currently available, conventional products attempt to automate renal artery image preparation and characterization, as a component of the abdominal aorta protocols. However, when these vessels are severely diseased, the software tracking routinely fails, and there is no easy way to compensate for this.

A dedicated protocol for the renal arterial system, as presently disclosed, addresses this problem. Automated analysis of the tomographic image data provides capability for efficiently deriving data analogous to that described above with reference to Table I et seq.

Figure 18:
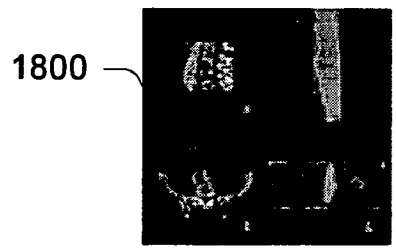
FIGS. 18 and 19 provide examples taken from collages of images (analogous to those shown above with reference to FIG. 9 et seq.) relating to protocols for characterization of renal vascularization, providing additional examples illustrating utility which the disclosed capabilities may provide when employed in the apparatus of FIG. 1.
Figure 19:
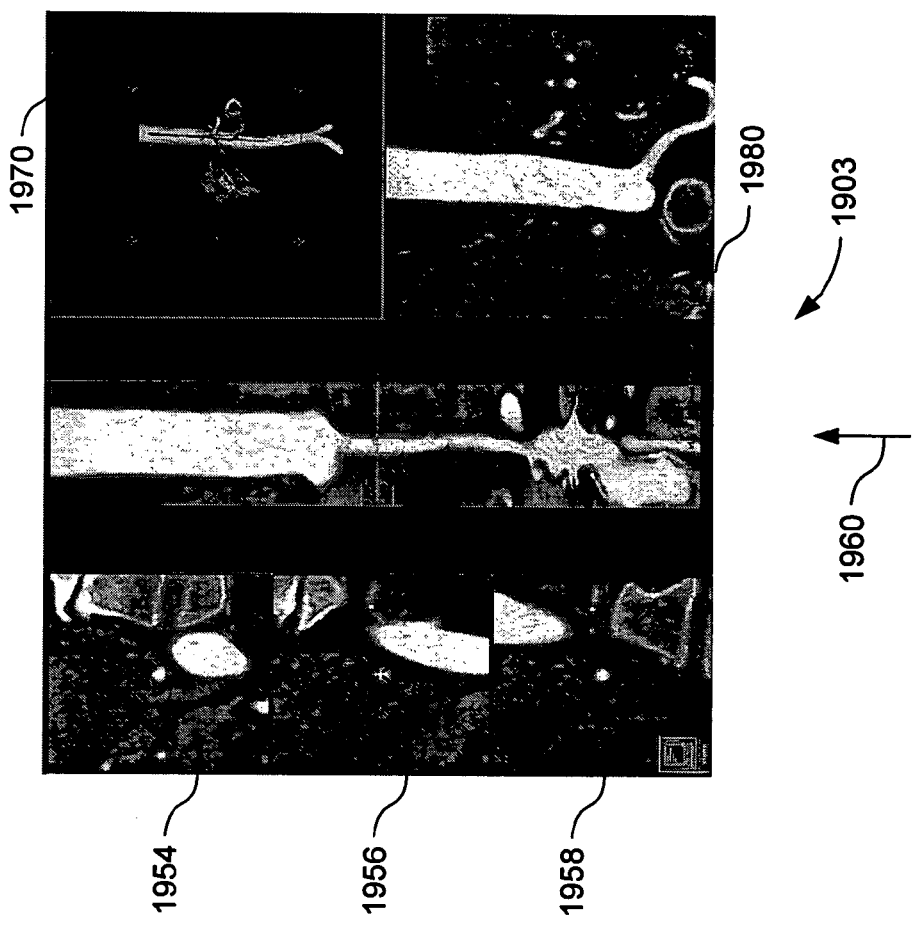
Figure 19:
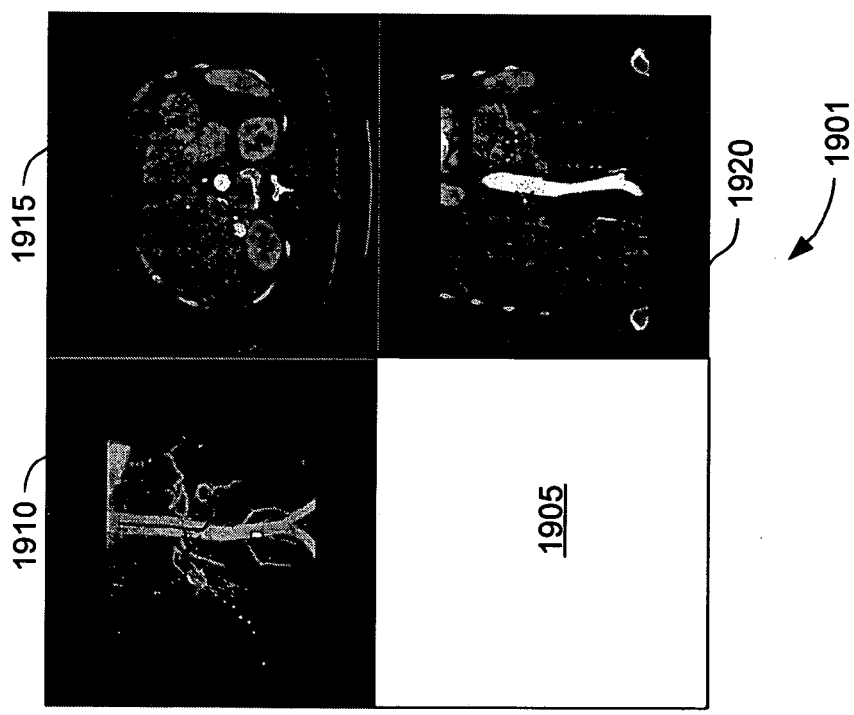

FIGS. 18 and 19 are composites 1800 and 1900 of several different image types for the renal arterial system, where the characterizations and the benefits of coordinating the images making up the various tiled images of FIGS. 18 and 19 are as described above with respect to the thoracic arterial characterizations. The renal arterial protocol, and images associated with it, may be recognized via association with the iconographic thumbnail 600 of FIG. 6, without reference to language-specific text.

FIG. 19 includes two panels 1901 and 1903, each including multiple views constructed from a body of imaging data. The panel 1901 includes, in addition to a control panel 1905, views 1910, 1915 and 1920. In the example of FIG. 19, the view 1910 is an image of the abdominal aorta system, showing the renal arteries in a three-dimensional or 3d MIP view. The view 1915 corresponds to an axial, "feet up" abdominal cross-sectional view, at the level of the liver. The view 1920 is a coronal view through the liver and the aorta system.

The panel 1903 includes a series of cross-sections 1954, 1956 and 1958, showing the arterial structure of interest at different positions along the length of the structure, and views 1960, 1970 and 1980. The view 1960 is a lumen view of the vessel of interest; the view 1970 represents a 3D VR rendering of the vascular structures being characterized; and the view 1980 is an example of a "curved" view. A curved view is one in which the data have been processed to provide an image corresponding approximately to what might result when a vessel has been "laid flat" on a planar surface; two-dimensional curvature is still present, in contrast to the lumen view 1960 and other views exemplified in this disclosure. The lumen views are also two-dimensional renderings of three-dimensional data, but have been treated to reduce the central area of the vessel as though it was a one-dimensional structure.

The renal arterial protocol allows the clinician to define, and thus place intermediate points along, the path describing the length of the renal artery, thus assisting the imaging engine 135 of FIG. 1 in the characterization process. As a result, a faster, more robust, reliable and repeatable characterization tool is provided for the clinician to accurately image the renal arterial system and to streamline and automate analysis issues pertaining to these vessels.

A group of exemplary vessel tracking points for the renal arterial characterization protocol is given below in Table VII below. In Table VII, the entries below "line" may correspond to lines as noted with reference to the control panel 1905 of FIG. 19, and described in more detail with reference to FIG. 24 infra, for example.

TABLE VII

Vessel Tracking points for Renal Arterial Protocol.

| Line | Measurement Points |
|---|---|
| 1 | Aorta - start of section |
| 2 | Right renal artery |
| 3 | Left renal artery |

§III(F). Mesenteric Artery Characterization Protocol Example

Figure 20:
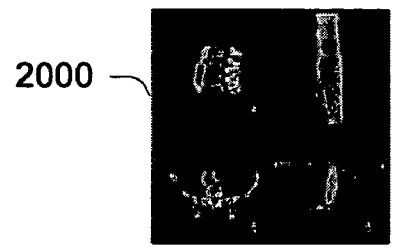
FIGS. 20 and 21 provide collages of images (analogous to those shown above with reference to FIG. et seq.) relating to protocols for characterization of mesenteric vascularization, providing additional examples illustrating utility which the disclosed capabilities may provide when employed in the apparatus of FIG. 1.
Figure 21:
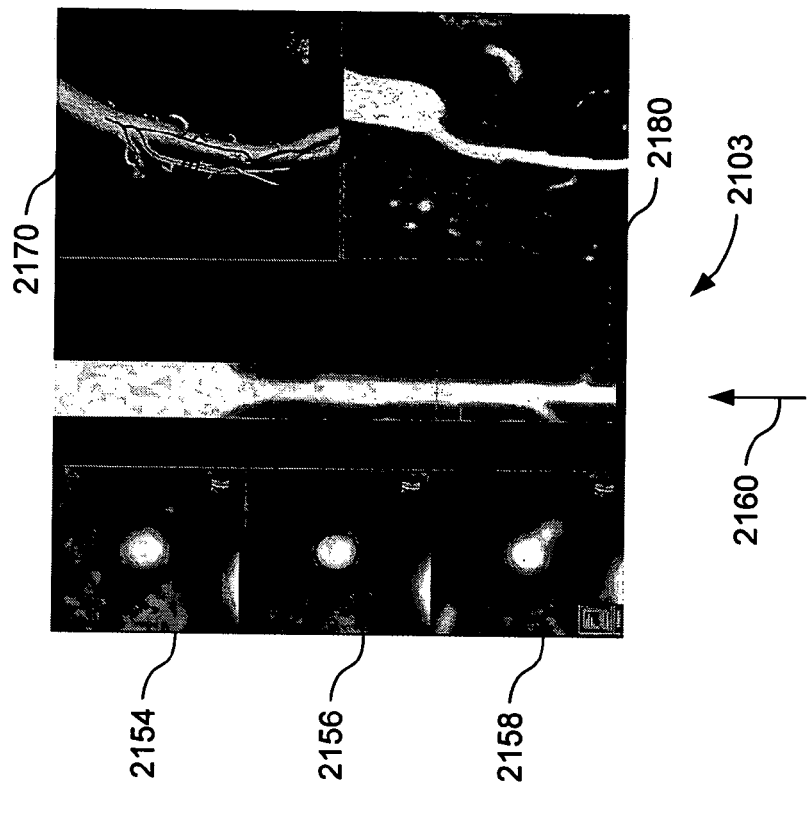
Figure 21:
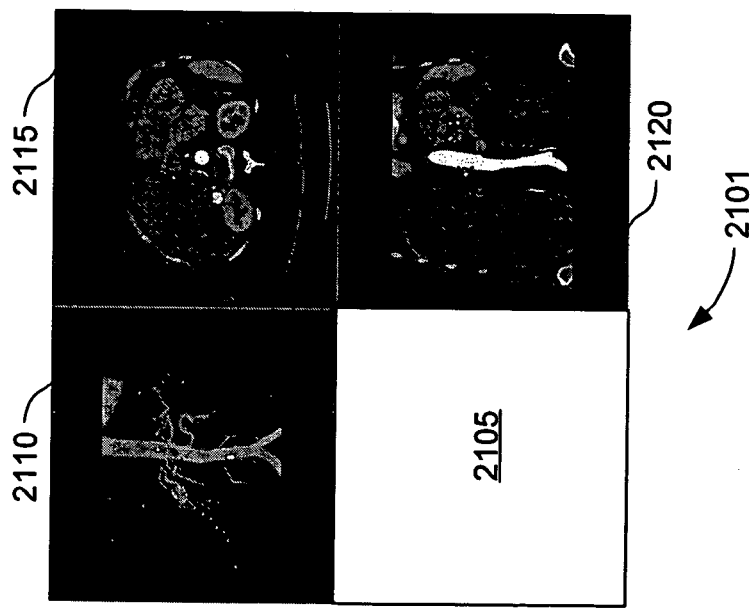

This protocol provides streamlined, anatomically-focused tools, specifically formulated for characterization and assessment of the arteries of the abdominal region providing blood supply to the mesentery and bowels. FIGS. 20 and 21 are composites 2000 and 2100, respectively, of several different image types for the mesenteric arterial system, where the characterizations and the benefits of coordinating the images making up the various tiled images of FIGS. 20 and 21, as described above with respect to the thoracic arterial characterizations. The mesenteric arterial protocol, and images associated with it, may be recognized in language independent manner, via association with the simplified representative image 700 of FIG. 7.

FIG. 21 includes two panels 2101 and 2103, each including multiple views constructed from a body of imaging data. The panel 2101 includes, in addition to a control panel 2105, views 2110, 2115 and 2120. The panel 2103 includes a series of cross-sections 2154, 2156 and 2158, and views 2160, 2170 and 2180. In the example of FIG. 21, the view 2110 is an image of the abdominal aorta system, showing the renal arteries in a three-dimensional or 3D MIP view. The view 2115 corresponds to an axial, "feet up" abdominal cross-sectional view, similar to the view 1915 of FIG. 19. The view 2120 is a coronal view through the liver and the mesenteric aorta system, which encompasses at least some portions of anatomy also relevant to the renal arterial protocol of subsection III(E).

The panel 2103 includes a series of cross-sections 2154, 2156 and 2158, showing the arterial structure of interest at different positions along the length of the structure, and views 2160, 2170 and 2180. The view 2160 is a lumen view of the vessel of interest; the view 2170 represents a 3D VR rendering of the vascular structures being characterized; and the view 2180 is curved view of the vascular vessel.

The mesenteric arterial characterization protocol facilitates identification of appropriate measurements for treatment, via identification and characterization of characteristic vessel tracking points. A group of vessel tracking points specific to the mesenteric arterial system is described by Table VIII below.

TABLE VIII

Vessel Tracking points for Mesenteric Arterial Protocol.

| Line | Measurement Points |
|---|---|
| 1 | Aorta - Start of Section |
| 2 | Celiac Artery |
| 3 | Superior Mesenteric Artery |
| 4 | Inferior Mesenteric Artery |

It will be appreciated that additional points may be appropriate, as noted above with respect to adding branches and addition of corresponding data entries and categories for anatomical structures that may be idiosyncratic to a specific patient or procedure.

§III(G). Protocol Customization Example

A clinician may adapt or build and customize the mesenteric protocol, or any other of the vessel analysis protocols disclosed herein, or later added to the automated data organization and characterization capabilities of the system 100 of FIG. 1, to fit anatomical idiosyncrasies specific to a particular patient. Each of the vessel analysis protocols described above with reference to subsections III(A) through III(F) includes a new vessel name database and suitable control buttons (e.g., such as buttons 212, 212', 212" of FIG. 2), providing data entry modification or augmentation points and thus allowing a clinician to add branching vascular structures with respect to a version of the appropriate protocols. Additionally, the clinician may similarly remove vascular structures from the protocol to fit the protocol to the presenting patient scenario, thereby customizing that protocol for anomalous findings. An exemplary table of specific (lines 1 through 14) and general (lines 15 through 22) entry points which the clinician might employ in such tailoring of protocol to individual patient needs appears below in Table IX.

TABLE IX

Exemplary entry points for customization of vessel analysis protocols.

| Line | New Label |
|---|---|
| 1 | Celiac Trunk |
| 2 | Superior Mesenteric Artery |
| 3 | Inferior Mesenteric Artery |
| 4 | Right Renal |
| 5 | Right Accessory Renal 1 |
| 6 | Right Accessory Renal 2 |
| 7 | Right Accessory Renal 3 |
| 8 | Left Renal |
| 9 | Left Accessory Renal 1 |
| 10 | Left Accessory Renal 2 |
| 11 | Left Accessory Renal 3 |

TABLE IX-continued

Exemplary entry points for customization of vessel analysis protocols.

| Line | New Label |
|------|-----------|
| 12 | Right External Iliac |
| 13 | Left External Iliac |
| 14 | End of Section |
| 15 | HEAD |
| 16 | NECK |
| 17 | CHEST |
| 18 | CARDIAC |
| 19 | SPINE |
| 20 | UPPER EXTREMITY |
| 21 | LOWER EXTREMITY |
| 22 | GENERAL |

Via selection of one or more entries from the list shown in Table IX for addition to a protocol, or deletion of one or more aspects of a protocol, a clinician is able to provide a customized version of the protocol. In turn, this facilitates automated data organization and analysis. Automated analysis of the tomographic image data provides capability for efficiently deriving data analogous to that described above with reference to Table I et seq.

§III(H). Post-Operative Evaluation Protocol Example

Figure 22:
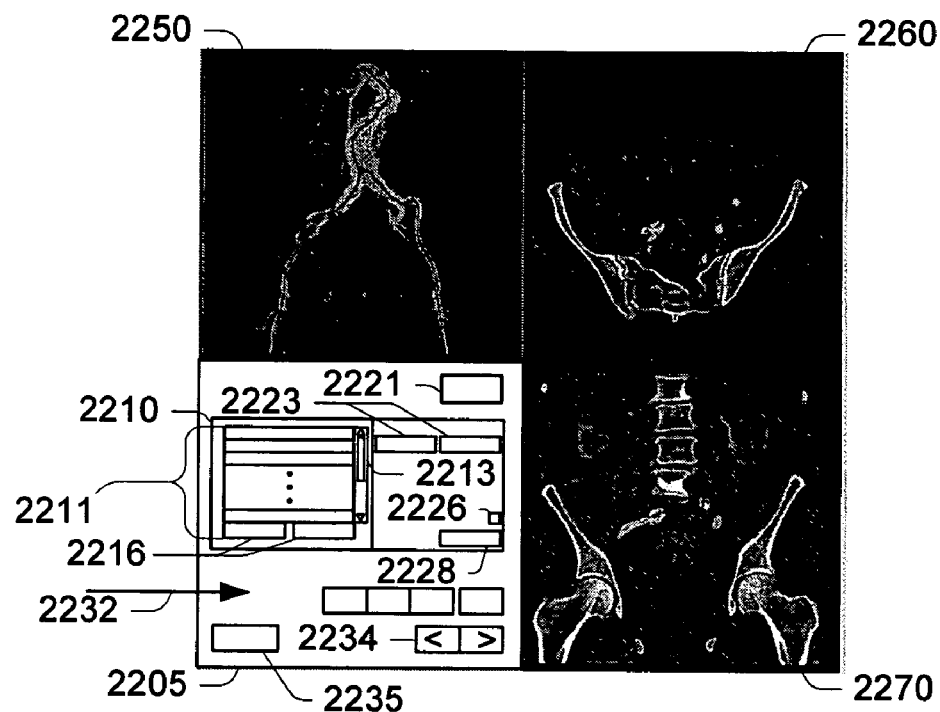
FIGS. 22 and 23 include a collection of images illustrative of a post-operative protocol for evaluation of aneurysm size, shifting of any implants, and the like, in accordance with an embodiment of the presently-disclosed subject matter, which is useful in the context of the system of FIG. 1.
Figure 23:
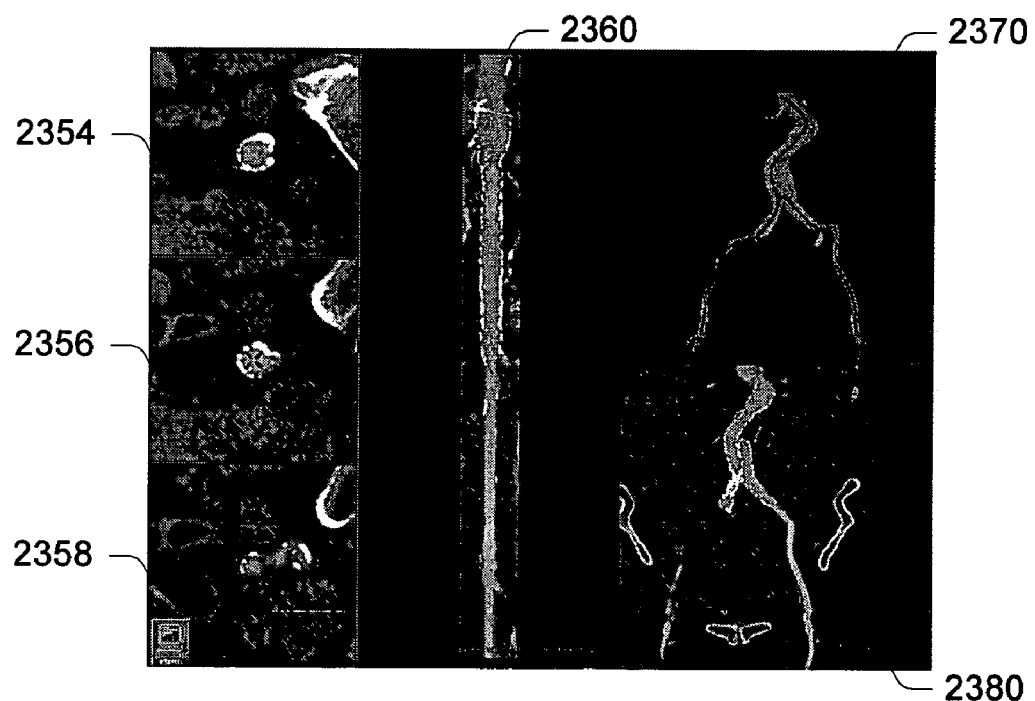

FIGS. 22 and 23 include collections 2200 and 2300, respectively, of images illustrative of a post-operative protocol for evaluation of aneurysm size, shifting of any implants, and the like, in accordance with an embodiment of the presently-disclosed subject matter, which is useful in the context of the system 100 of FIG. 1. The post-operative comparison protocol, and the images associated with it, may be recognized in language independent manner, via association with the simplified representative icon 800 of FIG. 8.

The images 2200 of FIG. 22 include a control panel or data entry and descriptor field 2205, which further includes a table or list 2210 of selected points within an image or body of data, as identified via text labels, for example, displayed via tabular entries 2211, and a scroll bar 2213, together with a number of function selection points.

In one embodiment, function buttons 2216 correspond to control functions CLEAR ALL (left button) and SHOW TRACES (right button). CLEAR ALL is an option allowing a clinician to "start over" with respect to selection and characterization of various vessel tracking points, while SHOW TRACES provides an option for tracking and reviewing vessel tracking points selected thus far, that is, prior to completion of point placement for the entire vascular system under study. In other words, SHOW TRACES provides the flexibility of a dynamic tracking option.

The control panel or data entry and descriptor field 2205 may also include one or more system control function buttons 2221, corresponding to VISUAL ANALYSIS SYSTEM PREFERENCES or HELP functions, for example. Additional control buttons 2223 may correspond to functions such as DEFINE BIFURCATIONS (self-explanatory) or START BRIDGE, for example.

A "check box" 2226, which may be selected or deselected via a tactile device interactively coupled to the display, or which may be employed via any other suitable input device, may correspond to turning ON or OFF an option such as USE MULTIPLE POINTS in forming the assessment. START BRIDGE refers to an option, selectable via the USE MULTIPLE POINTS selection tool 2226, whish may be relevant when a vessel presents anomalies precluding automated tracking. In many protocols, tracking proceeds via confirmation of a distal vessel tracking point and then follows a path conforming to predetermined selection rules. As an example, contrast levels between the vessel walls and the interior of the vessel may be used in conjunction with thresholds to present a tracking display for review and approval or revision by a clinician.

However, these thresholds or other criteria may be obscured or unavailable in some situations. For example, a vessel which is completely occluded may fail to provide sufficient contrast for the resulting image data to be reliable in the context of automated tracing through the length of the vessel. As a result, the clinician may wish to be able to place vessel tracking points at locations such as at each end of such an anomaly, and utilize those in a manner where these points are "linked"—providing a "trail of bread crumbs" allowing the anomaly to be "bridged" by the automated assessment tools, and thus facilitating relevant characterization.

A control button 2228 may correspond to a CORRECT BRANCH function. The CORRECT BRANCH function simply allows the last vessel tracking point selected to be re-selected, for example, responsive to review via the SHOW TRACES capability described above with reference to the control button 2216.

A series of control buttons 2232 may allow a clinician to select options such as ADD BRANCH, RENAME BRANCH, REMOVE BRANCH and SAVE PROTOCOL, for example. A control function area 2234 may facilitate moving to another portion of the protocol, such as allowing the clinician to move BACK or to select a NEXT frame in the protocol. A control button 2235 may allow the clinician to opt to hide one or more views or panels via a HIDE PANELS feature. Analogous control and labeling functions may also be associated with the control panels 1905 and 2105 of FIGS. 19 and 21, respectively, albeit in conjunction with modifications which may be specific to a particular protocol, either preprogrammed, or as adapted by a clinician.

FIG. 23 includes a series of cross-sections 2354, 2356 and 2358, and views 2360, 2370 and 2380. The view 2360 is an example of a lumen view. FIGS. 22 and 23 exemplify the types of images or data 2200 and/or 2300 which may be compared to prior groups of such images or data to assess changes in conditions over time.

The post-operative protocol may be specifically designed for clinicians to analyze an aorta after surgery or other intervention. For example, the post-operative protocol may be employed for analysis of an abdominal aorta after a stent has been implanted.

In some conventional systems, when a physician needs to diagnose implant position, such as to determine when a stent has migrated or shifted in position from one imaging process or CT scan to another, or later, imaging process or CT scan, a very time-consuming, tedious, manual process is required. Further, this is getting more so with the explosion of data which imaging systems are able to provides, such as CT slices, and the volume of data the clinician must sort through. Clinicians involved in carrying out these types of interventional procedures need a streamlined, fast, and easy-to-use protocol for measuring the aorta and delivering an accurate diagnosis.

The disclosed protocol responds to these needs, and thus improves clinician productivity and confidence, resulting in a faster diagnosis, and in improved treatment for the patient. The disclosed post-operative protocol may be used for any post-surgical vessel analysis, for example, in conjunction with evaluation of an aorta to quantify any stent or implant shifting and/or any aneurysm volume changes.

This protocol also provides key measurements to analyzing stent posture to detect shifting or migration, following surgical emplacement of a stent in the abdominal aorta. Among other things, this protocol quickly and efficiently provides diagnostic information as to whether or not the stent has shifted position. Table X below enumerates some useful measurements which are automatically derived via the disclosed protocol.

TABLE X

Exemplary characteristics assessed for post-stent/implant arterial protocols.

| Measurement Points | Aspect characterized |
|---|---|
| Lowest Renal to Superior Stent Margin | Length |
| Lowest Renal to Inferior Stent Margin | Length |
| Stent Height | Length |
| Inferior Stent Margin to Right Iliac Bifurcation | Length |
| Inferior Stent Margin to Left Iliac Bifurcation | Length |
| Superior Stent Margin at proximal attachment site | Diameter |
| Superior to Inferior Stent Margin (Aortic Stent) | Length |
| Right Iliac Stent* | Length |
| Left Iliac Stent* | Length |

*Aortic Bifurcation to Iliac Inferior Margin of Stent Point

§III(I). Viewing Modality Examples

Figure 24:
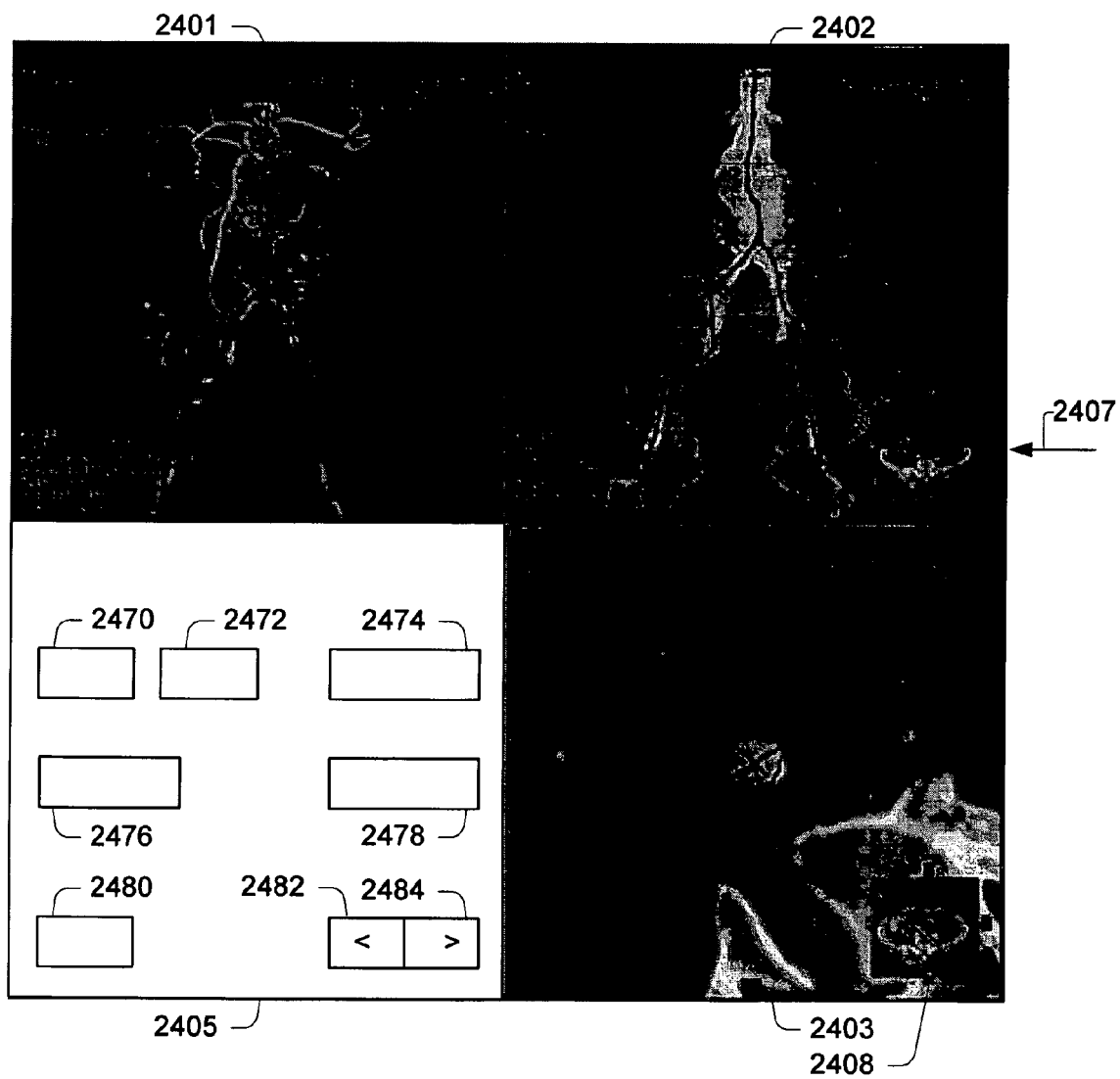
FIGS. 24 and 25 provide ensembles of linked pictorial representations in accordance with an embodiment of the presently-disclosed subject matter, constructed from imaging information provided via non-destructive imaging techniques, after processing and analysis in, and in accordance with, the image and data processing and display apparatus and modalities of the present disclosure, which data organizational, analysis and presentation capabilities find utility in the system of FIG. 1.
Figure 25:
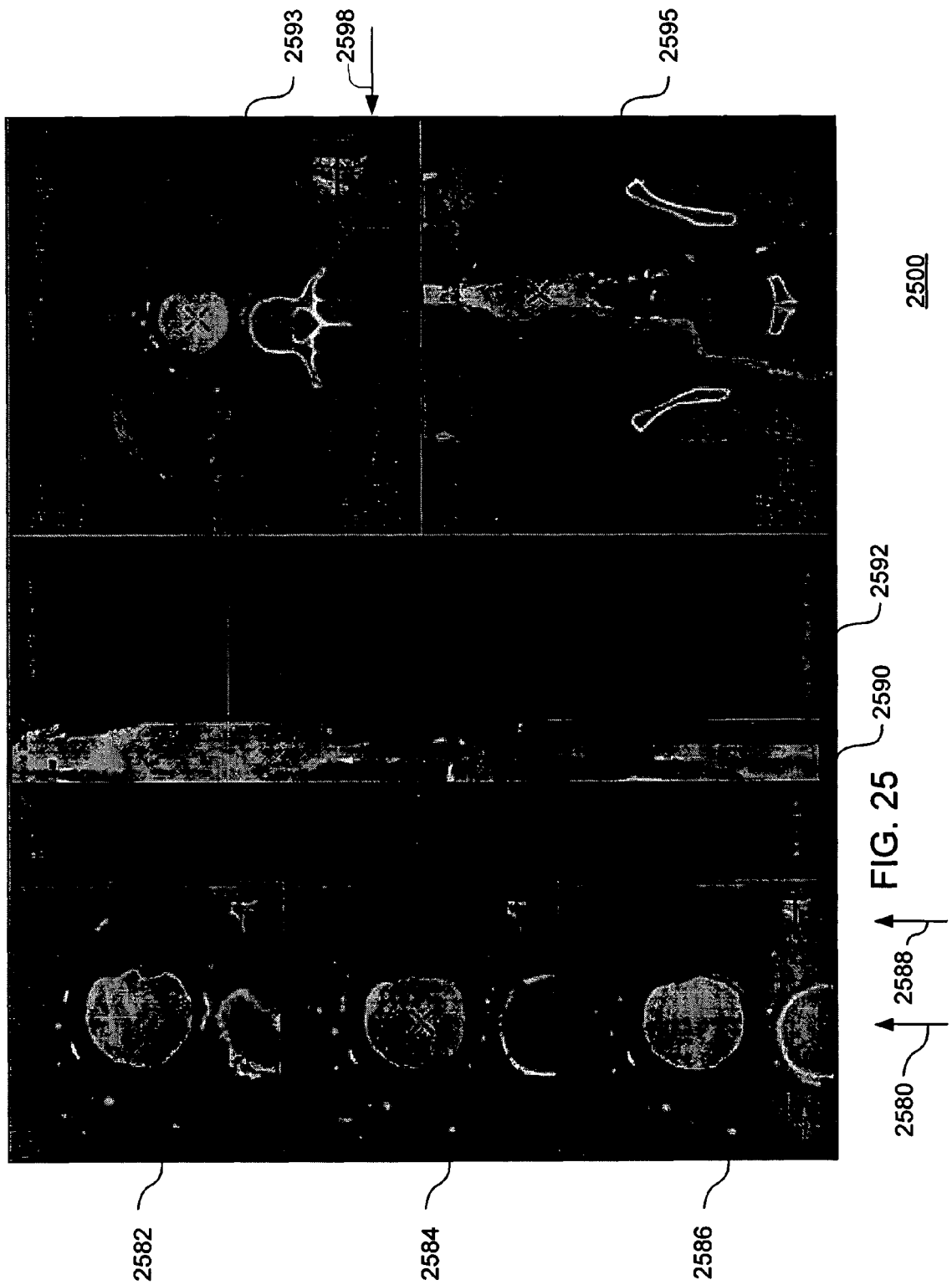
Figure 26:
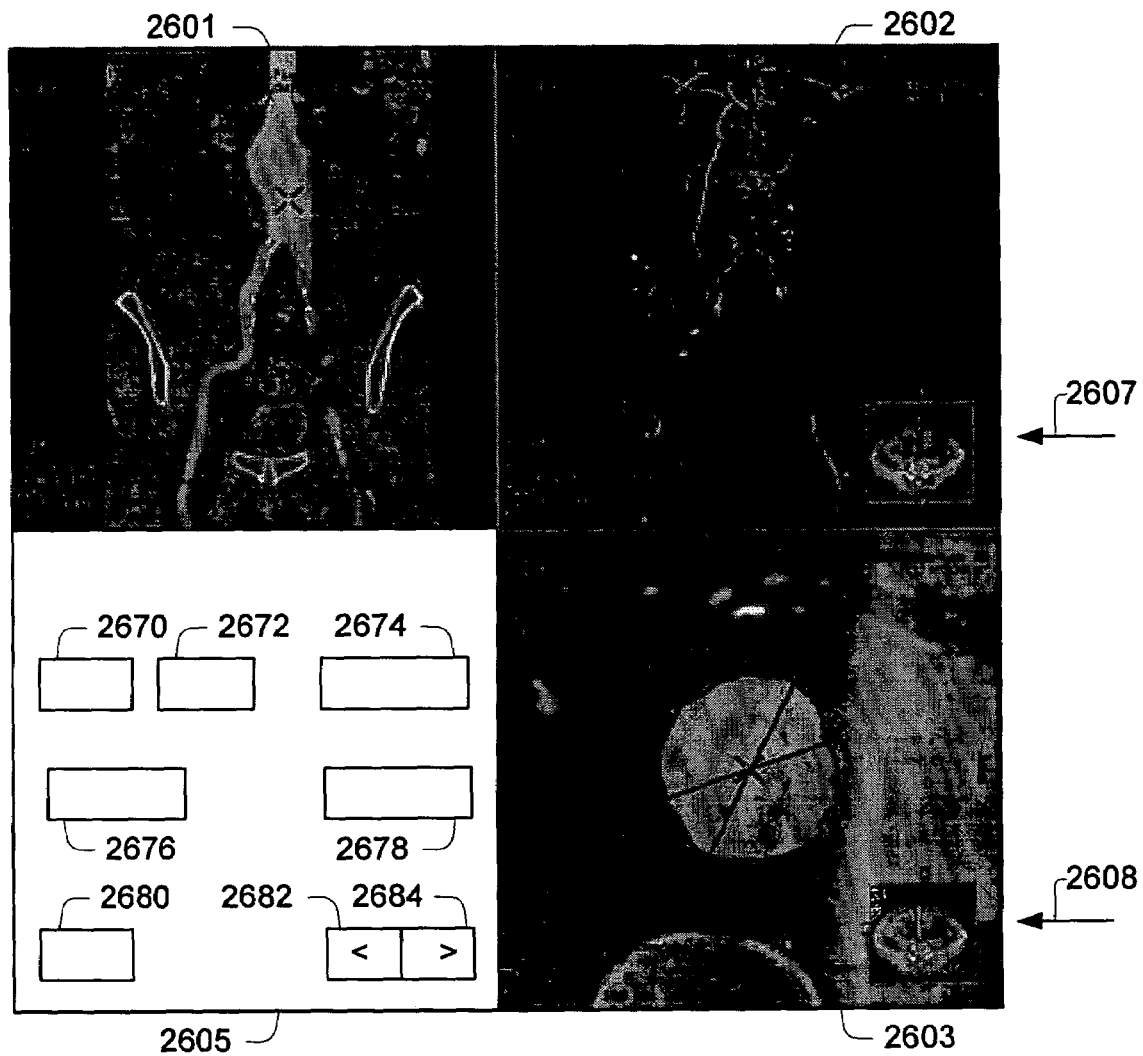
FIGS. 26 and 27 illustrate linked groups of graphical images in accordance with an embodiment of the presently-disclosed subject matter, the images having been developed by processing of non-destructive imaging information via the disclosed image and data processing and display apparatus and modalities, demonstrating a form in which the disclosed capabilities find utility in the context of the X-ray tomographic data collection and analysis equipment of FIG. 1.
Figure 27:
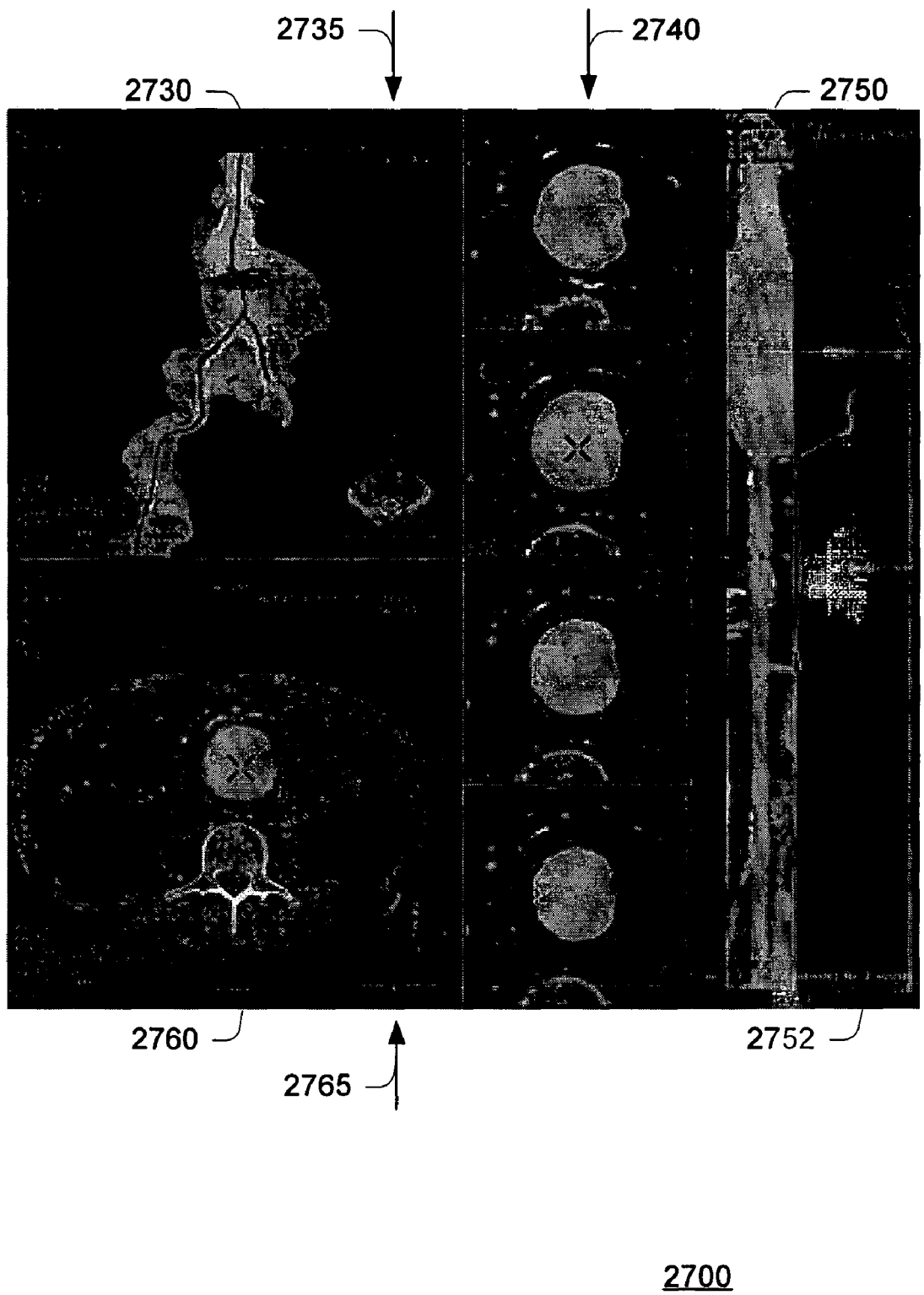
Figure 28:
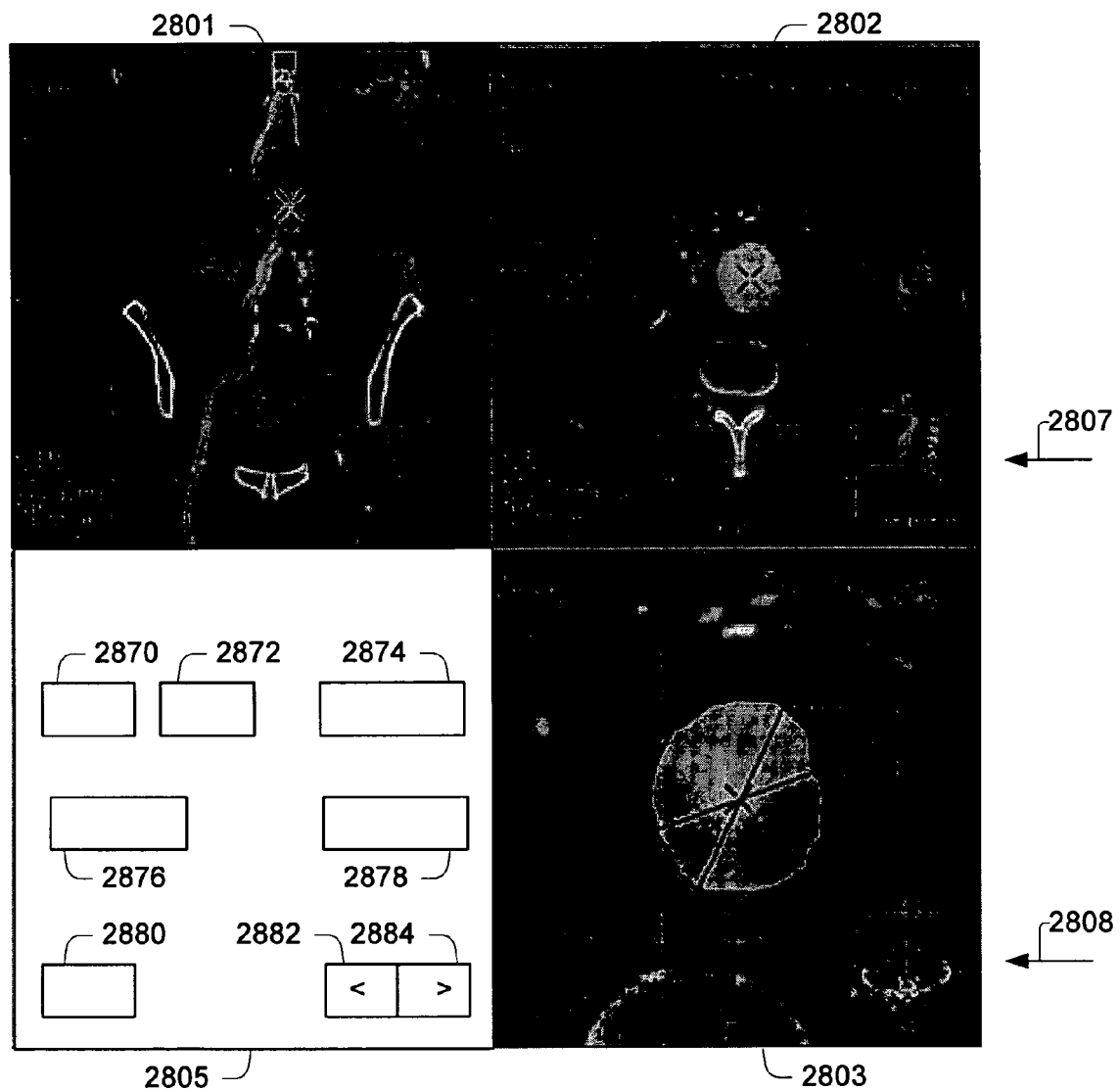
FIGS. 28 and 29 illustrate multiple tesselations of linked anatomical representations in accordance with an embodiment of the presently-disclosed subject matter, constructed from tomographic imaging information, after processing by the image and data processing engine of the present disclosure, showing a form in which these capabilities find utility in the context of the apparatus of FIG. 1.
Figure 29:
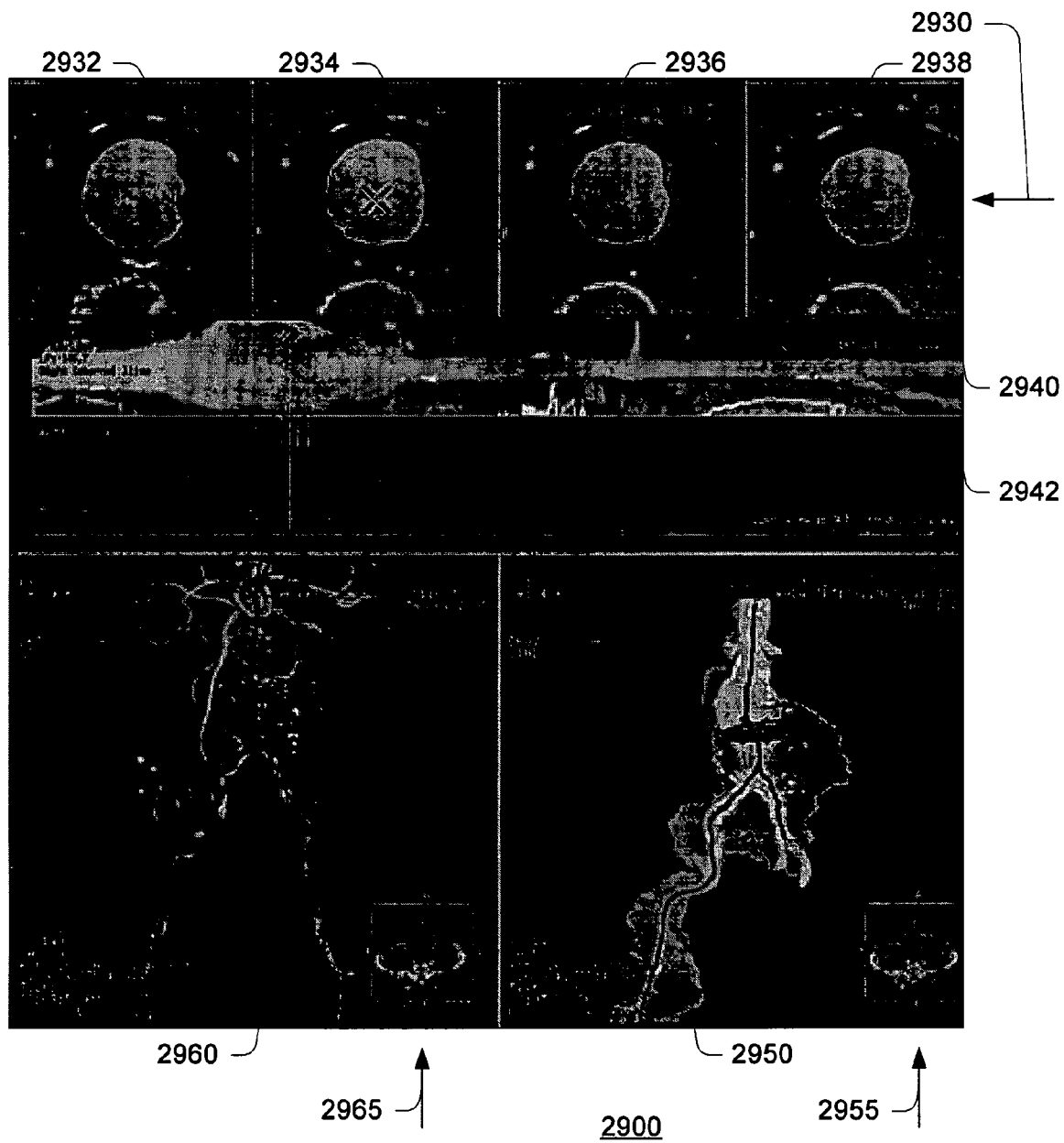

FIGS. 24 and 25 provide image groups 2400 and 2500, respectively, showing an exemplary embodiment of a viewing modality for coordination of a plurality of different images formed from a common body of tomographic data through one or more of the displays 142 of FIG. 1. FIGS. 26 and 27 display similar view collages 2600 and 2700, respectively, illustrative of an embodiment, while FIGS. 28 and 29 illustrate analogous tesselations of anatomical representations 2800 and 2900, respectively. In turn, characterization of images formed from the tomographic data that is stored in a memory, such as the memory devices 150 of FIG. 1, is facilitated.

The composite images 2400 of FIG. 24 include a first image 2401, a second image 2402, and a third image 2403 (analogous to image fields or panels I, II and III of FIG. 2, respectively), and a control panel 2405. Insets 2407 (in image 2402) and 2408 (in image 2403) show relationships between the images and the diseased tissue being studied. The images 2401, 2402, 2403, 2405, 2407 and 2408 are collectively tessellated to provide the collage 2400.

The first image 2401 corresponds to a three-dimensional volume rendering of a vascular system. The second image 2402 is an example of a three-dimensional MIP display constructed from the same tomographic data as the image 2401. The third image 2403 depicts an oblique view that also is produced using the image processing engine 135 of FIG. 1 from the same body of image data points as the images 2401 and 2402.

The control panel 2405 provides convenient access to a number of user-selectable features via graphically-depicted buttons amenable to user selection through tactile or other input devices 144. Alternative user selection tools may also be contemporaneously available (e.g., keyboard entries on a menu-type format, etc.) and the user may employ multiple input-output modes during a single viewing and analysis procedure. In other words, the user may opt to enter some selections via a mouse or touchscreen, by selecting functions through the control panel 2405, while providing input regarding other selections through another input-output tool at the same time. Entry of numerical data, for example, may be more efficiently accomplished through a keyboard and a different viewing aspect, which may be co-displayed on the same monitor 142 or via a different monitor 142 or display.

The control panel example 2405 of FIG. 24 includes memory and editing functions applicable to one or both of the image groups 2400 of FIG. 24 and 2500 of FIG. 25. The types of functions that may be accessed through control features of the control panel example 2405 may include a variety of functions such as SAVE STATS 2470, COMPARE 2472 and EDIT 2474 control buttons. Also included are characterization and assessment function buttons, such as COLOR IDENTIFICATION 2476 and EXTRACT THROMBUS 2478 controls.

The control panel example 2405 also may include procedural control buttons, such as HIDE PANELS 2480, and BACK 2482 and NEXT 2484 controls, for example. In one embodiment, the control panel 2405 may include controls for: (i) editing or modifying a central axis of a vessel that is being characterized, such as with respect to the lumen view 2590; (ii) modification of cross-sectional views 2580 (e.g., the separations between the slices 2582, 2584, 2586, such as location of one or more of the cross-sectional views 2580); (iv) initiation of a new measurement or characterization; (v) EDIT, UNDO or ACCEPT functions, and the like. The disclosed image processing engine 135, however, is capable of coordination of editing functions for: (a) any one, (b) any selected ones or (c) all of the views shown in the composite displays 2400 and/or 2500, with the clinician being able to select among options (a), (b) or (c), as or when appropriate.

FIG. 25 includes a series 2580 of other views, viz., sequential cross sections or slices 2582, 2584 and 2586, insets 2588, a lumen view 2590 side-by-side and coordinated with a graph 2592 showing degree of blockage, an axial view 2593 with inset 2594, and a curved view 2595, all contemporaneously and automatically constructed by the image processing engine 135 from the same tomographic data as the images 2401, 2402, 2403, 2407 and 2408 of FIG. 24. The insets 2588 and 2594 illustrate relationships between the various views and the diseased tissue/region under study.

The lumen view 2590 is adjacent the graph 2592 displaying estimated degree of blockage (more blockage corresponding to excursion of the trace on the graph 2592 to the right) vs. length along the selected vascular element. The lumen view 2590 and graph 2592 are correlated and show (near the top) a region of blockage, which is where the axial sections are taken from (faint horizontal lines on left side of the lumen, and horizontal line extending to the trace on the graph 2592 on the right). The curved view 2595 corresponds to an image constructed by the image processing engine 135 of FIG. 1 to provide an "unkinked" or straightened version of the vascular system being studied.

FIGS. 26 and 27 provide another exemplary embodiment of a viewing modality for coordination of a plurality of different images 2600, 2700 formed from a common body of tomographic data through one or more of the displays 222 of FIG. 1. In turn, characterization of images formed from the tomographic data stored in a memory, such as the memory devices 150 of FIG. 1, is facilitated.

The composite images 2600 of FIG. 26 include a first image 2601, a second image 2602, and a third image 2603 (analogous to image fields or panels I, II and III of FIG. 2, respectively), a control panel 2605, and insets 2607 (in image 2602) and 2608 (in image 2603). These are collectively tiled to provide the ensemble 2600, with the insets 2607 and 2608 depicting relationships between the images and the region being studied.

In the viewing modality shown in FIG. 26, the first image 2601 corresponds to a curved rendering of a vascular system. The second image 2602 is an example of a three-dimensional volume rendering display constructed from the same tomographic data as the image 2601. The third image 2603 depicts an oblique image that also is produced using the image processing engine 135 of FIG. 1 from the same body of image data points as the images 2601 and 2602.

FIG. 27 includes a three-dimensional MIP image 2730 with an inset 2735, a sequence 2740 of sequential cross sections or slices, a lumen view 2750 coordinated with an adjacent graph 2752 illustrating estimated blockage (with more blockage corresponding to excursion of the trace to the right), and an axial view 2760 together with an inset 2765, all contemporaneously and automatically constructed by the image processing engine 135 from the same tomographic data as the images 2601, 2602, 2603, 2607, 2608 of FIG. 26.

The control panel example 2605 of FIG. 26 includes memory and editing functions analogous to those described above with reference to FIG. 24 and which are operative to affect the composite images 2600 of FIG. 26 and/or 2700 of FIG. 27, or selected subsets of one or more of such. These functions may be nominally identical to those described above, such as SAVE STATS 2670, COMPARE 2672, EDIT 2674, COLOR IDENTIFICATION 2676, EXTRACT THROMBUS 2678, HIDE PANELS 2680, and BACK 2682 and NEXT 2684 controls, for example. However, it will be appreciated that more or fewer function modification access points or features may be included, as appropriate, and that the range of such features may be modified over time, for example in the manner described below with reference to the process 3000 of FIG. 30 in Section IV.

FIGS. 28 and 29 provide another exemplary embodiment of a viewing modality for coordination of a plurality of different images 2800, 2900 formed from a common body of tomographic data in a manner similar to that described above with reference to FIGS. 24, 25 and 26, 27.

The multiple image views 2800 of FIG. 28 include a first image 2801, a second image 2802, and a third image 2803 (analogous to image fields or panels I, II and III of FIG. 2, respectively), a control panel 2805, inset 2807 (in image 2802) and inset 2808 (in image 2803), joined to form the composite image 2800, with the insets 2807 and 2808 depicting relationships between the images and the region being studied.

In the viewing modality shown in FIG. 28, the first image 2801 corresponds to a curved rendering of a vascular system. The second image 2802 is an example of an axial display constructed from the same tomographic data as the image 2801. The third image 2803 depicts an oblique image that also is derived using the image processing engine 135 of FIG. 1 from the same image data points as the images 2801 and 2802.

The control panel example 2805 of FIG. 28 includes memory and editing functions analogous to those described above with reference to FIGS. 24 and 26. These may be nominally identical, such as SAVE STATE 2870, COMPARE 2872, EDIT 2874, COLOR IDENTIFICATION 2876, EXTRACT THROMBUS 2878, HIDE PANELS 2880, and BACK 2882 and NEXT 2884 controls, for example.

FIG. 29 includes a sequence 2930 of sequential cross sections or slices 2932, 2934, 2936, 2938, a lumen view 2940 together with a graph 2942 illustrating estimated blockage (with vertical excursion of the trace corresponding to more blockage), a three-dimensional MIP image 2950 with inset 2955, and a three-dimensional volume rendering image 2960 with inset 2965, all contemporaneously and automatically constructed by the image processing engine 135 from the same tomographic data as the images 2801, 2802, 2803, 2807 and 2808 of FIG. 28.

It can be appreciated that while the total data content for each of these three viewing modalities are very similar, the order and the way in which the various images are provided differs from one viewing modality to another. Some of the differing ways in which the images are displayed modifies relative placement, facilitating visual juxtapositions, and thus presents relationships between different images facilitating different "eyeball" comparisons; others rotate the more elongated representations by ninety degrees. Each viewing modality thus places different emphases on relationships between the various images.

As a result, a clinician has a variety of options for use in efficiently reviewing multiple coordinated views of a region being characterized. Consequently, the clinician is able to, for example, confirm that the image processing engine 135 of FIG. 1 has correctly identified a sequence of vessel tracking points, for example as enumerated in the Tables associated with the respective protocols described above, and can do so with increased confidence, as well as improved accuracy.

Process embodiments operative with the system 100, together with benefits associated with their cooperative engagement, are described below in more detail in Section IV, with reference to FIGS. 30 and 31.

§IV. Process Embodiments

In the previous section, protocols developed in furtherance of functionality with respect to system modifications were disclosed and described. In this section, the developments and adaptations of Section III are further employed as vehicles for describing the operation of a series of embodiments, with the particular processes of such embodiments being described by reference to relevant flowcharts (FIGS. 30, 31). Describing the processes by reference to one or more flowcharts enables one skilled in the art to develop programs, firmware, or hardware, including such instructions configured to effectuate the processes, as well as subsequent revisions, through one or more processors responsive to computer-readable instructions embodied on computer-readable media.

These capacities are often accomplished using suitable computers, including one or more processors, by executing instructions embodied in articles of manufacture such as computer-readable media, or as modulated signals embodied in a carrier wave. As a result, the computer-readable instructions may include capacity for accepting revised computer-readable information descriptive of revised capabilities, which may relate to revisions of aspects of the system 100 via substitution of components, revisions of data-processing structures and the like. Similarly, processes performed by server computer programs, firmware, or hardware also are represented by computer-executable instructions. The processes of the present disclosure are performed by one or more program modules executing on, or performed by, firmware or hardware that is a part of a computer (e.g., computer 130, FIG. 1).

In some embodiments, processes 3000, 3100 disclosed herein are implemented as a computer data signal embodied in a carrier wave that represents a sequence of instructions which, when executed by one or more processors, such as a processor contained in or associated with the computer 130 in FIG. 1, causes the respective process to occur. As a result, protocols such as those exemplary anatomically-specific characterization procedures described above with reference to §III may be augmented or revised, for example by downloading suitable software modifications via a network such as a LAN, a WAN, a storage area network, or the Internet, and thus capable of affecting the functionality provided via the image processing engine 135 of FIG. 1. Revisions, modifications and the like also may be effectuated via other media suitable for storage, exchange, restoration or augmentation of computer-readable and computer-executable program elements.

In some embodiments, the processes 3000, 3100 are implementable via computer-accessible media storing executable instructions capable of directing processor units, such as one or more processors contained in or associated with the computer 130 in FIG. 1. In varying embodiments, the medium is a magnetic medium, an electronic medium, or an electromagnetic/optical medium.

More specifically, in a computer-readable program embodiment, programs can be structured in an object-orientation using an object-oriented language such as Java, Smalltalk or C++, and the programs can be structured in conformance with a procedural-orientation using a procedural language such as COBOL or C. Software components may communicate in any of a number of ways that are well-known to those skilled in the art, such as application program interfaces (API) or interprocess communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer (e.g., computer 130, FIG. 1), or on multiple computers.

The three exemplary viewing modalities described above in subsection III(G) allow the clinician to select a modality fitting the clinician's preferences and that is suitable for the procedure being performed, examples of which are described above with reference to subsection III(B) et seq. The viewing modalities each provide a process for displaying and evaluating data stored in memory from a tomographic examination. The flexibility provided via user selection among multiple viewing modalities for analysis of data that are stored in memory, and the coordination between the plurality of views and formats provided by the image processing engine 135 of FIG. 1, streamlines the review and characterization of the data.

Figure 30:
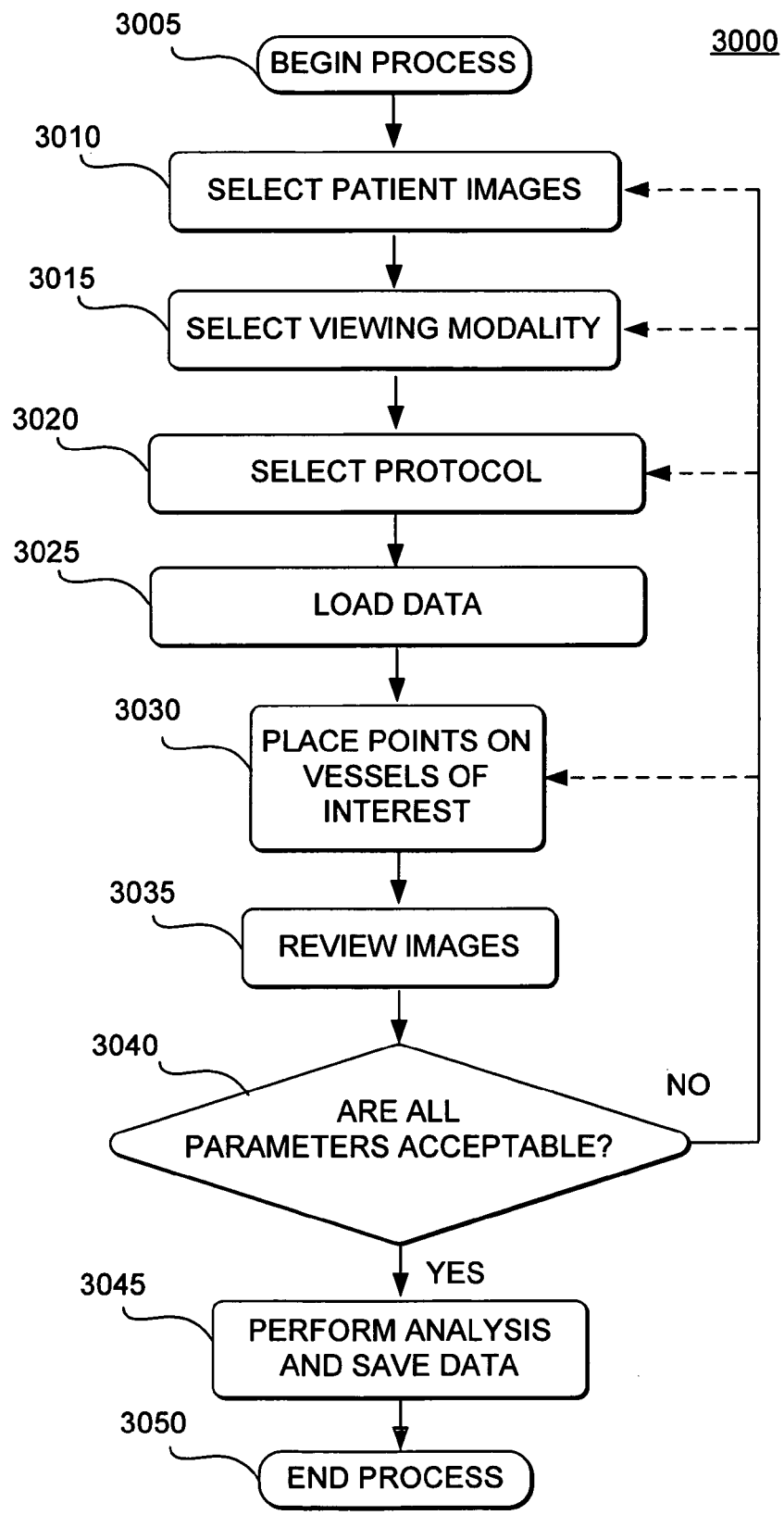
FIGS. 30 and 31 are flowcharts describing processes capable of utility in the system of FIG. 1.
Figure 31:
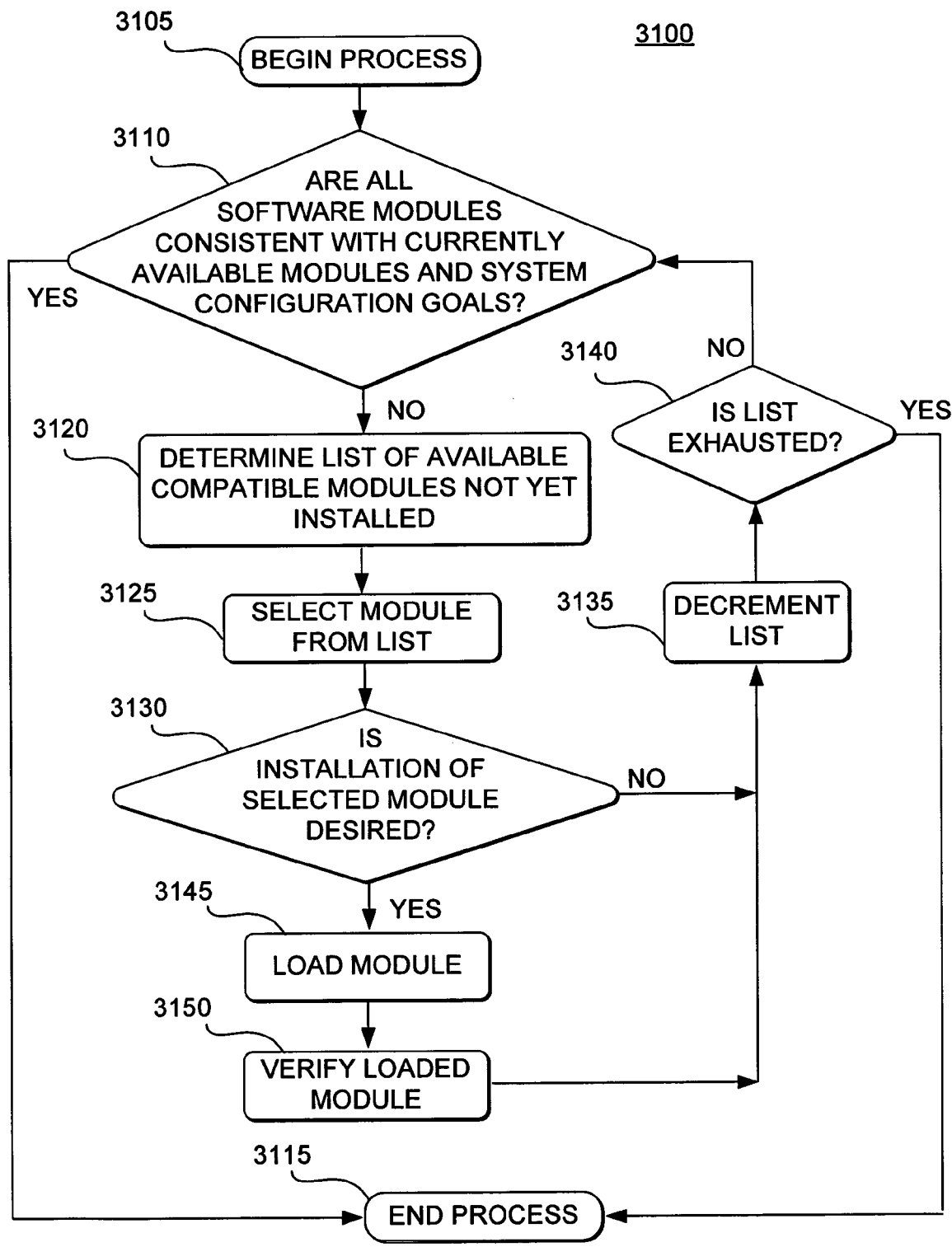

FIGS. 30 and 31 are flowcharts describing processes 3000 and 3100, respectively, which are capable of utility in the system 100 of FIG. 1. The process 30000 of FIG. 30 shows a way of implementing the protocols of the present disclosure, while the process 3100 of FIG. 31 illustrates one mode for updating of the software for the overall system 100.

FIG. 30 is a flowchart describing a process 3000 for protocol actualization that is capable of utility in the system 100 of FIG. 1. The process 3000 begins in a block 3005.

In a block 3010, the process 3000 allows a clinician to select a body of data that provide capability for generation of relevant patient images. Control then passes to a block 3015.

In the block 3015, the clinician selects a viewing modality. Non-limiting examples of such are described above with reference to subsection III(G), however, it will be appreciated that other types of viewing modalities are also possible. Control then passes to a block 3020.

In the block 3020, the clinician selects a protocol. Non-limiting examples of such protocols are described above with reference to subsection III(B) et seq. and FIG. 9 et seq. Control then passes to a block 3025.

In the block 3025, the data selected in the block 3010 are loaded into the appropriate software modules in conformance with the selections made in the block 3020. Control then passes to a block 3030.

In the block 3030, the clinician reviews the images displayed as a result of the various parameters selected in the preceding blocks. One benefit to the disclosed subject matter relative to prior art is that the curved, and oblique, images are generated "up front"—and automatically—from the data by the image processing engine 135 of FIG. 1, thereby streamlining the tasks that are placed before the clinician and thus promoting efficiency.

The clinician then either confirms or modifies points which may have been automatically selected, or employs a cursor or other input-output modality for specifying or modifying selected points. Examples of suitable points include the vessel tracking points provided above with reference to tabular data associated with the respective protocols. Control then passes to a block 3035.

In the block 3035, the clinician reviews images representative of the patient data and of the selections made in the preceding blocks. The review of images carried out in conjunction with the block 235 may include review of all of the images being synthesized, or such might involve review of some or all images then on screen or may involve review of a "signature" image known to be indicative of the quality and spread of data required for the task or tasks associated with the types of characterization etc. to which the imaging data are appropriate. Control then passes to a query task 3040.

The query task 3040 determines when the parameters and characteristics reviewed in the block 3035 are acceptable. The query task 3040 may also compare the selections to predetermined out-of-range or unsuitable selection indicia, or otherwise predetermined criteria reflecting an inappropriate or possibly inappropriate set of selection criteria.

When the query task 3040 determines that not all of the parameters being reviewed appear to be acceptable, control passes back to either the block 3030 (reflecting an inappropriate choice of points for characterization), the block 3020 (reflecting an inappropriate protocol selection), the block 3015, reflecting either an inappropriate viewing modality selection or simply a desire by the clinician to review the information in conformance with another viewing modality, or to the block 3010, reflecting a desire to select a different set of patient images or in an event where it is desirable to review the selections of the process 3000 from an early point in the process. Such might reflect a desire to compare two datasets from the same patient, but at different times, or any of many other types of decision-making processes. Control then iterates through the process 3000 as described above.

When the query task 3040 determines that all parameters are acceptable, control passes to a block 3045. In the block 3045, the data are analyzed to provide the characterizations desired. The results of the process 3000 are then saved to memory, such as the memory 150 of FIG. 1. Control then passes to a block 3050, and the process 3000 then ends.

FIG. 31 is a flowchart of a process 3100 for realization of a mode in which software updates and modifications may be implemented in the system 100 of FIG. 1. The process 3100 begins in a block 3105.

In a query task 3110, the process 3100 determines when all of the software modules contained in the system 100 are consistent with the collection of presently-available software modules and with the current-applicable configuration goals for the system. A variety of factors may have resulted in a change in either the range of software modules available or in the configuration goals presently desired. For example, addition of new hardware may result in desire to expand the library of protocols in order to realize benefits provided through the revised hardware configuration or upgrade. New surgical procedures and tools may give rise to new assessment protocols and revised output data requirements.

When the query task 3110 determines that the software modules presently actualized through the system 100 are consistent with configuration goals and include all relevant software modules and updates, control passes to a block 3115, and the process 3100 ends. When the query task 3110 determines that the software modules presently actualized through the system 100 are not necessarily consistent with configuration goals and or do not necessarily include all relevant software modules and updates, control passes to a block 3120.

In the block 3120, a list of available software modules that are capable of compatibility in the context of the system 100 and the system configuration goals is prepared. Control then passes to a block 3125.

In the block 3125, one or more software modules are selected from the list compiled in the block 3120. In one embodiment, the software module or modules are selected from a display of a list extracted from the list compiled in the block 3120. In one embodiment, a next available example of a software module taken from the list assembled in the block 3120 is automatically selected and the selection is displayed to a system maintenance person. Control then passes to a query task 3130.

The query task 3130 determines when installation of the selected module or modules may be desirable. When the query task 3130 determines that installation of the selected module or modules is desirable, control passes to a block 3145. When the query task 3130 determines that installation of the selected module or modules is not desirable, control passes to a block 3135.

In the block 3135, the list is decremented. In other words, the selected module or modules are removed from the list assembled in the block 3120. Control then passes to a query task 3140.

The query task 3140 determines when the list initially assembled in the block 3120 has been exhausted. When the query task 3140 determines that the list has been exhausted, control passes to the block 3115, and the process 3100 ends. When the query task 3140 determines that the list has not been exhausted, control passes back to the query task 3110 (or to the block 3120). One reason for contemplating passing control back to the query task 3110 is that as the complement of software modules and capabilities changes with changing software population of the system 100, the implications of compatibilities and needs may change.

For example, a module for comparison of results for two types of analysis would be irrelevant until such point as software modules supporting both of the two types of analysis are present, and that, in turn, may be a function of selections made earlier, in the block 3125. This could occur when a hardware modification is capable of supporting more than one mode of operation is being addressed, but only modules corresponding to a portion of those modes are selected for actualization—in that hypothetical situation, it would not be apparent initially that the comparison module might be desired.

When the query task 3130 determines that installation of the selected module or modules is desirable, control passes to the block 3145. In the block 3145, the selected module or modules are loaded or installed. Control then passes to a block 3150.

In the block 3150, the module or modules that had been loaded in the block 3145 are verified. For example, a first check is to ensure that loading was complete and accurate. Also, compatibility of the loaded module or modules, as implemented, with other system elements may need to be verified. Control them passes to the block 3135 and the process 3100 iterates as described above.

It will be appreciated that the process 3100 may be implemented in a number of different ways. For example, a qualified party may supervise downloading of appropriate modules via a modulated carrier wave, such as a signal transmitted via a network such as the Internet. Alternatively, a memory module may be added to the memory 150 of FIG. 1, such as a CD or solid state ROM, or a removable data storage device 158 may be coupled to the removable storage device port 156 to download selected data groups as desired.

Accordingly, the process 3000 of FIG. 30 may be updated via addition or substitution of machine-readable and executable instructions in computer-based controllers, as is described above with reference to the process 3100, and also below in Section V, with reference to FIG. 32.

As a result, the system 100 is provided with revised data and instructions. Capabilities of the system 100 are augmented. As an example, a technical effect promoted by such can include capability of transmission, via digital technologies, of radiographic images having improved diagnostic value for immediate contemplation and evaluation by experts during triage, or even during transportation of a victim of an accident from the situs of the disaster to suitable medical facilities—such as during the "golden moments" immediately following determination of injury that are extremely vital to increasing patient survival, as well as recovery trajectory. These features and advantages can represent significant improvements in system performance, from a capabilities perspective as well as reliability considerations. Such enhancements, in terms of machine-controlled performance in tandem with operator review and approval, may be achieved via the elements described above with reference to FIGS. 1 through 20, as well as in conjunction and cooperation with an operating environment such as that which is described below in Section V with reference to FIG. 32.

§V. Hardware and Operating Environment

Figure 32:
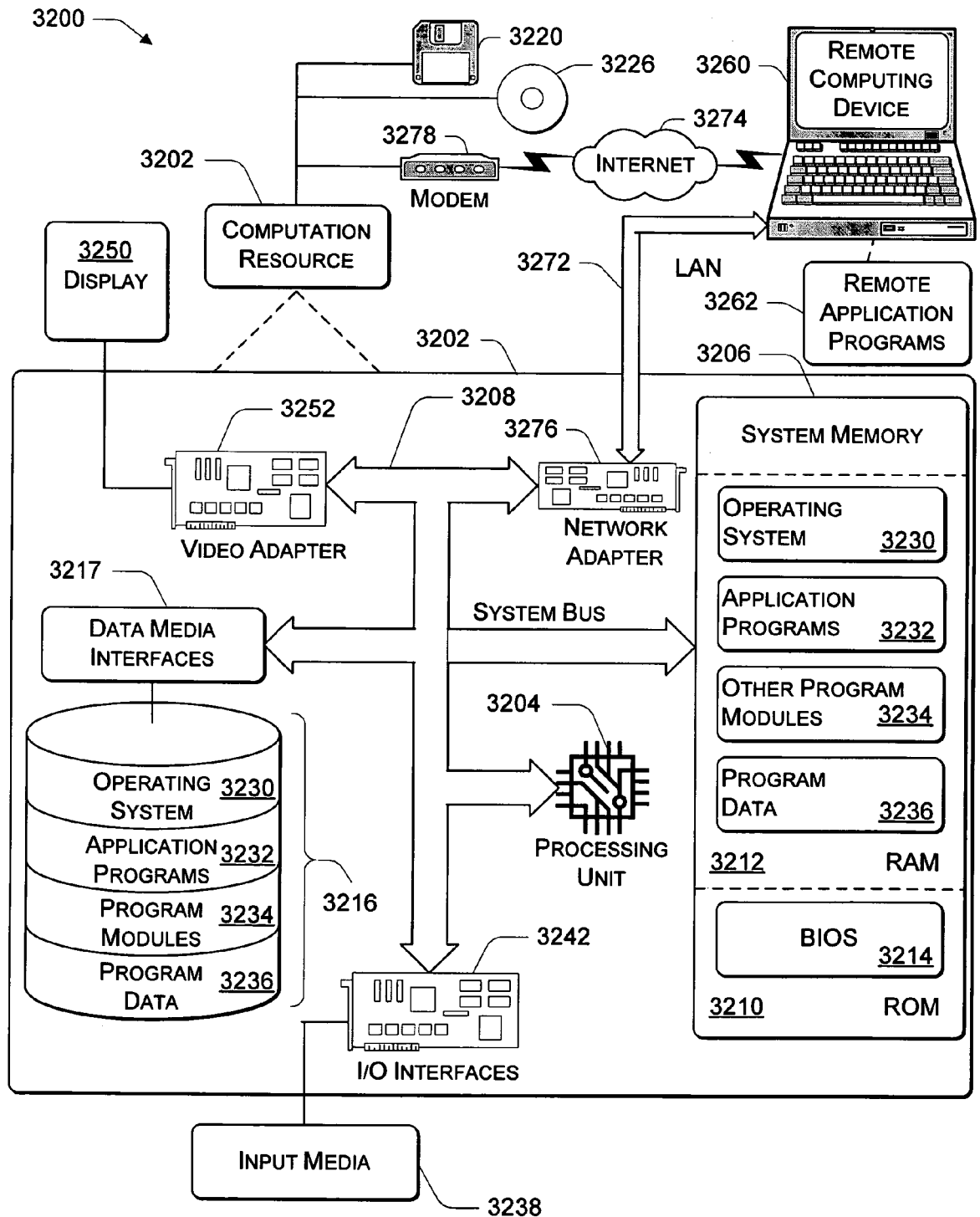
FIG. 32 illustrates an example of a general computation resource useful in the context of the environment of FIG. 1.

FIG. 32 illustrates an example of a general computer environment 3200 that includes a computation resource 3202 capable of implementing the processes described herein. It will be appreciated that other devices may alternatively used that include more components, or fewer components, than those illustrated in FIG. 32. The illustrated operating environment 3200 is only one example of a suitable operating environment, and the example described with reference to FIG. 32 is not intended to suggest any limitation as to the scope of use or functionality of the embodiments of this disclosure. Other well-known computing systems, environments, and/or configurations may be suitable for implementation and/or application of the subject matter disclosed herein.

The computation resource 3202 includes one or more processors or processing units 3204, a system memory 3206, and a bus 3208 that couples various system components including the system memory 3206 to processor(s) 3204 and other elements in the environment 3200. The bus 3208 represents one or more of any of several types of bus structures, including a memory bus or memory controller, a peripheral bus, an accelerated graphics port and a processor or local bus using any of a variety of bus architectures, and may be compatible with SCSI (small computer system interconnect), or other conventional bus architecture and protocol. The system memory 3206 includes nonvolatile read-only memory (ROM) 3210 and random access memory (RAM) 3212, which may or may not include volatile memory elements. A basic input/output system (BIOS) 3214, containing the elementary routines that help to transfer information between elements within computation resource 3202 and with external items, typically invoked into operating memory during start-up, is stored in ROM 3210.

The computation resource 3202 further may include a non-volatile read/write memory 3216, represented in FIG. 32 as a hard disk drive, coupled to bus 3208 via a data media interface 3217 (e.g., a SCSI, ATA, or other type of interface); a magnetic disk drive (not shown) for reading from, and/or writing to, a removable magnetic disk 3220 and an optical disk drive (not shown) for reading from, and/or writing to, a removable optical disk 3226 such as a compact disc or CD, DVD, or other optical media.

The non-volatile read/write memory 3216 and associated computer-readable media provide nonvolatile storage of computer-readable instructions, data structures, program modules and other data for the computation resource 3202. Although the exemplary environment 3200 is described herein as employing a non-volatile read/write memory 3216, a removable magnetic disk 3220 and a removable optical disk 3226, it will be appreciated by those skilled in the art that other types of computer-readable media which can store data that is accessible by a computer, such as magnetic cassettes, FLASH memory cards, random access memories (RAMs), read only memories (ROM), and the like, may also be used in the exemplary operating environment.

A number of program modules may be stored via the non-volatile read/write memory 3216, magnetic disk 3220, optical disk 3226, ROM 3210, or RAM 3212, including an operating system 3230, one or more application programs 3232, other program modules 3234 and program data 3236. A user may enter commands and information into computation resource 3202 through input devices such as input media 3238 (e.g., keyboard/keypad, tactile input or pointing device, mouse, foot-operated switching apparatus, joystick, touchscreen or touchpad, microphone, antenna etc.). Such input devices 3238 are coupled to the processing unit 3204 through an input/output interface 3242 that is coupled to the system bus (e.g., a serial port interface, a parallel port interface, a universal serial bus (USB) interface, an IEEE 1354 (Firewire) interface, etc.). A monitor 3250 or other type of display device is also coupled to the system bus 3208 via an interface, such as a video adapter 3252.

The computation resource 3202 may include capability for operating in a networked environment (as illustrated in FIG. 1, for example) using logical connections to one or more remote computers, such as a remote computer 3260. The remote computer 3260 may be a personal computer, a server, a router, a network PC, a peer device or other common network node, and typically includes many or all of the elements described above relative to the computation resource 3202. In a networked environment, program modules depicted relative to the computation resource 3202, or portions thereof, may be stored in a remote memory storage device such as may be associated with the remote computer 3260. By way of example, remote application programs 3262 reside on a memory device of the remote computer 3260. The logical connections represented in FIG. 32 may include a storage area network (SAN, not illustrated in FIG. 32), local area network (LAN) 3272 and/or a wide area network (WAN) 3274, but may also include other networks.

Such networking environments are commonplace in modern computer systems, and in association with intranets and the Internet. In certain embodiments, the computation resource 3202 executes an Internet Web browser program (which may optionally be integrated into the operating system 3230), such as the "Internet Explorer" Web browser manufactured and distributed by the Microsoft Corporation of Redmond, Wash.

When used in a LAN-coupled environment, the computation resource 3202 communicates with or through the local area network 3272 via a network interface or adapter 3276. When used in a WAN-coupled environment, the computation resource 3202 typically includes interfaces, such as a modem 3278, or other apparatus, for establishing communications with or through the WAN 3274, such as the Internet. The modem 3278, which may be internal or external, is coupled to the system bus 3208 via a serial port interface.

In a networked environment, program modules depicted relative to the computation resource 3202, or portions thereof, may be stored in remote memory apparatus. It will be appreciated that the network connections shown are exemplary, and other means of establishing a communications link between various computer systems and elements may be used.

A user of a computer may operate in a networked environment 100 using logical connections to one or more remote computers, such as a remote computer 3260, which may be a personal computer, a server, a router, a network PC, a peer device or other common network node. Typically, a remote computer 3260 includes many or all of the elements described above relative to the computer 3200 of FIG. 32.

The computation resource 3202 typically includes at least some form of computer-readable media. Computer-readable media may be any available media that can be accessed by the computation resource 3202. By way of example, and not limitation, computer-readable media may comprise computer storage media and communication media.

Computer storage media includes volatile and nonvolatile, removable and non-removable media, implemented in any method or technology for storage of information, such as computer-readable instructions, data structures, program modules or other data. The term "computer storage media" includes, but is not limited to, RAM, ROM, EEPROM, FLASH memory or other memory technology, CD, digital versatile disks (DVD) or other optical storage, magnetic cassettes, magnetic tape, magnetic disk storage or other magnetic storage devices, or any other media which can be used to store computer-intelligible information and which can be accessed by the computation resource 3202.

Communication media typically embodies computer-readable instructions, data structures, program modules or other data, represented via, and determinable from, a modulated data signal, such as a carrier wave or other transport mechanism, and includes any information delivery media. The term "modulated data signal" means a signal that has one or more of its characteristics set or changed in such a manner as to encode information in the signal in a fashion amenable to computer interpretation.

By way of example, and not limitation, communication media includes wired media, such as wired network or direct-wired connections, and wireless media, such as acoustic, RF, infrared and other wireless media. The scope of the term computer-readable media includes combinations of any of the above.

The computer 3202 may function as one or more of the control segments of module 120 (FIG. 1), the computer 130, the operator console 140 and/or the data acquisition and conditioning module 160, for example, via implementation of the processes 3000 and 3100 of FIGS. 30 and 31 as computer program modules.

§VI. Conclusion

A computer-based medical imaging system is described. Although specific embodiments have been illustrated and described herein, it will be appreciated by those of ordinary skill in the art that any arrangement which is calculated to achieve the same purpose may be substituted for the specific embodiments shown. This disclosure is intended to cover any adaptations or variations. For example, although described in procedural terms, one of ordinary skill in the art will appreciate that implementations can be made in a procedural design environment or any other design environment that provides the required relationships.

In particular, one of skill in the art will readily appreciate that the names or labels of the processes and apparatus are not intended to limit embodiments. Furthermore, additional processes and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types. The terminology used in this disclosure is meant to include all object-oriented, database and communication environments and alternate technologies which provide the same functionality as described herein.

What is claimed is:

1. A process for selecting a protocol to provide coordinated view and characterization of an anatomical region in a nondestructive imaging system, the process comprising:
   receiving a body of data to generate relevant images for the anatomical region;
   selecting an anatomically specific protocol from a group of anatomically specific protocols, each anatomically specific protocol of the group being structured to provide multiple coordinated views of a particularized anatomical region and to facilitate automated characterization of an aspect of the anatomical region;
   opting for at least one of a plurality of viewing modalities for review of images associated with the selected anatomically specific protocol; and
   displaying the images in conformance with the at least one viewing modality, the displayed view of each of the images being in a panel, the panel including a series of cross-sections showing a structure of interest at different positions along the length of the structure, and views, a first view being a lumen view, the lumen view being a two-dimensional rendering of three-dimensional data of the structure of interest and treated to reduce the central area of the structure as though the structure was a one-dimensional structure, a second view representing a 3D VR rendering of the structure being characterized; and a third view being a curved view, the curved view being an image corresponding approximately to the anatomical region being laid flat on a planar surface wherein two-dimensional curvature is still present.

2. The process of claim 1, wherein the nondestructive imaging system comprises an X-ray system, and wherein the images are constructed by an image processing engine from tomographic data.

3. The process of claim 1, wherein the selecting an anatomically specific protocol from a group of anatomical protocols further comprises:
   selecting the anatomically specific protocol from a group consisting of: a thoracic aorta characterization protocol; a bilateral carotid artery characterization protocol; a renal artery characterization protocol and a mesenteric artery characterization protocol.

4. The process of claim 1, wherein the selected anatomically specific protocol provides measurements for a stent, responsive to a clinician designating a sequence of points along an artery being characterized.

5. The process of claim 1, wherein the anatomically specific protocols and viewing modalities available may be altered via modification of software.

6. The process of claim 1, wherein, following the selecting and opting, the process further comprises:
   placing points on vessels of interest via the images;
   reviewing the images and placements;
   performing an analysis to provide data characterizing the vessels of interest; and
   recording the data in a memory.

7. The process of claim 1, wherein, following the selecting and opting, the process further comprises:
   placing points on vessels of interest via the images;
   reviewing the images and placements;
   performing an analysis to provide data characterizing the vessels of interest, the data including sizing parameters for a stent; and
   saving the data in a memory.

* * * * *